United States Patent [19]

Nishizawa et al.

[11] Patent Number: 4,943,567
[45] Date of Patent: Jul. 24, 1990

[54] CEPHALOSPORIN COMPOUND AND PHARMACEUTICAL COMPOSITION THEREOF

[75] Inventors: Susumu Nishizawa, Kyoto; Hiroyuki Muro, Higashiazai; Masayasu Kasai; Satoru Hatano, both of Kameoka; Syouzi Kamiya, Kyoto; Nobuharu Kakeya, Nagaokakyo; Kazuhiko Kitao, Kyoto, all of Japan

[73] Assignee: Kyoto Pharmaceutical Industries, Ltd., Kyoto, Japan

[21] Appl. No.: 228,714

[22] Filed: May 27, 1988

[30] Foreign Application Priority Data

May 30, 1987 [JP] Japan .................. 62-136647

[51] Int. Cl.$^5$ .................. A61K 31/545; C07D 501/20
[52] U.S. Cl. .................. 514/203; 514/204; 514/206; 514/207; 540/222; 540/225; 540/227; 540/228
[58] Field of Search ............... 540/222, 225, 227, 228; 514/203, 204, 206, 207

[56] References Cited

U.S. PATENT DOCUMENTS 4,370,326  1/1983  Takaya et al. .................. 540/222
4,372,952  2/1983  Takaya et al. .................. 540/222
4,487,767 12/1984  Takaya et al. .................. 540/227

*Primary Examiner*—Nicholas S. Rizzo
*Assistant Examiner*—Andrew G. Rozycki
*Attorney, Agent, or Firm*—Berman, Aisenberg & Platt

[57] ABSTRACT

Cephalosporin compounds represented by the general formula (I):

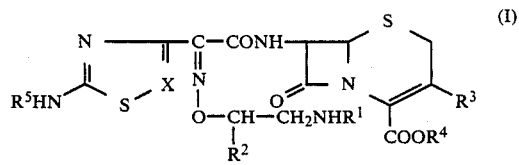

wherein $R^1$ and $R^5$ independently represent a hydrogen atom or a protective group for an amino group; $R^2$ represents an alkyl group or a cycloalkyl group; $R^3$ represents a hydrogen atom, a lower alkenyl group, an alkanoyloxymethyl group, a carbamoyloxymethyl group, a heterocyclic thiomethyl group or a heterocyclic methyl group; $R^4$ represents a hydrogen atom or an ester residue; and X represents CH or a nitrogen atom and pharmacologically acceptable addition salts thereof, intermediate compounds used in the synthesis process of these compounds, production methods of these compounds and pharmaceutical compositions containing these compounds.

Said compounds or addition salts thereof exhibit noticeable antibacterial activities even on Pseudomonas aeruginosa, on which known cephalosporin compounds do not exhibit antibacterial activities, and moreover, work well against ordinary Gram-positive bacteria and Gram-negative bacteria.

15 Claims, No Drawings

CEPHALOSPORIN COMPOUND AND PHARMACEUTICAL COMPOSITION THEREOF

FIELD OF THE INVENTION

The present invention relates to new cephalosporin compounds and pharmacologically acceptable addition salts thereof (which have a broad antibacterial spectrum and are very effective specifically on Pseudomonas bacteria), intermediate compounds for the synthesis of these compounds, production methods of these compounds, pharmaceutical compositions containing these compounds and methods for the treatment of bacterial infectious diseases.

BACKGROUND OF THE INVENTION

The cephalosporin compounds are useful compounds having antibacterial activities. Active studies have been made on their synthesis, and many compounds have already been produced. Some of them now occupy clinically important positions as antibiotics having a broad antibacterial spectrum.

In general, most of the broad-spectrum cephalosporin antibiotics now in use in clinical situations have hardly any antibacterial activity against Pseudomonas bacteria, while those having antibacterial activities against Pseudomonas bacteria are slightly effective on Gram-positive bacteria, Gram-negative bacteria, and the like. That is, there has not yet been discovered any broad-spectrum cephalosporin antibiotic having antibacterial activities against all of these bacteria. Accordingly, any of the broad-spectrum cephalosporin antibiotics, for example, cefzonam, flomoxef and ceftazidime, are either ineffective on Pseudomonas bacteria or weak in antibacterial activities on other bacteria even when they are effective on Pseudomonas bacteria.

Accordingly, an object of the present invention is to provide cephalosporin antibiotics having a broad antibacterial spectrum and noticeable antibacterial activity against Gram-positive bacteria, Gram-negative bacteria, etc. as well as against Pseudomonas bacteria.

Another object of the present invention is to provide production methods for making said cephalosporin antibiotics.

A further object of the present invention is to provide intermediate compounds for the production of said cephalosporin antibiotics.

A further object of the present invention is to provide pharmaceutical compositions containing said cephalosporin antibiotics.

A further object of the present invention is to provide methods for the treatment of bacterial infectious diseases by administration of said cephalosporin antibiotics.

SUMMARY OF THE INVENTION

The present inventors made studies to accomplish the above purposes, and thus found that cephalosporin compounds represented by the general formula:

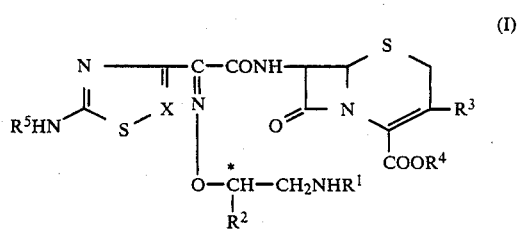

(wherein $R^1$ and $R^5$ independently represent a hydrogen atom or a protective group for an amino group; $R^2$ represents an alkyl group or a cycloalkyl group; $R^3$ represents a hydrogen atom, a lower alkenyl group, an alkanoyloxymethyl group, a carbamoyloxymethyl group, a heterocyclic thiomethyl group or a heterocyclic methyl group; $R^4$ represents a hydrogen atom or an ester residue; and X represents =CH— or a nitrogen atom, or pharmacologically acceptable addition salts thereof) have a broad antibacterial spectrum and possess noticeable antibacterial activity against Gram-positive bacteria, Gram-negative bacteria, etc., as well as against Pseudomonas bacteria, specifically Pseudomonas aeruginosa. The present inventors made further studies based on this finding, and completed the present invention.

Accordingly, the present invention relates to the cephalosporin compounds (I) and pharmacologically acceptable addition salts thereof, intermediate compounds used in the synthesis of these compounds, production methods of making these compounds, pharmaceutical composition containing these compounds and methods for the treatment of infectious diseases.

The cephalosporin compounds (I) of the present invention and pharmacologically acceptable addition salts thereof are characterized by the presence of a substituent having the definition for $R^2$ above and bonded to the α-position carbon atom adjacent to the oxime's oxygen atom in general formula (I). A noticeably broad spectrum of antibacterial activities, as mentioned above, is not possessed by any of the compounds having no substituent for $R^2$ at the above-mentioned α-position carbon atom adjacent to the oxime's oxygen atom in general formula (I) or of the compounds having a substituent for $R^2$ both at the β-position carbon atom and the above-mentioned α-position carbon atom adjacent to the oxime's oxygen atom; therefore, it is really surprising that the cephalosporin compounds (I) and pharmacologically acceptable addition salts thereof have the above-mentioned unique antibacterial activity.

DETAILED DESCRIPTION OF THE INVENTION

As an alkyl group for $R^2$ in the present specification, a lower alkyl group having from 1 to 4 carbon atoms is preferred, and its examples include methyl, ethyl, propyl, isopropyl, butyl, sec-butyl and t-butyl. As a cycloalkyl group for $R^2$, a cycloalkyl group having from 3 to 6 carbon atoms is preferred, and its examples include cyclopropyl and cyclobutyl.

As a lower alkenyl group for $R^3$, a lower alkenyl group having from 2 to 4 carbon atoms is preferred, and its examples include vinyl, 1-propenyl and 2-propenyl.

As the alkanoyl moiety in the alkanoyloxymethyl group for $R^3$, an alkanoyl group having from 2 to 4 carbon atoms is preferred, and its examples include acetyl and propionyl.

Furthermore, a heterocycle in a heterocyclic thiomethyl group for $R^3$ is exemplified by 5- or 6-membered heterocycles which preferably contain from 1 to 4 nitrogen atoms in their ring and which may further contain sulfur atom(s) or oxygen atom(s). Specific examples of such heterocycles include 2-, 3- or 4- pyridyl, N-oxide-2-, 3- or 4-pyridyl, 2-, 4- or 5-thiazolyl, 2-, 4- or 5-oxazolyl, 3-, 4- or 5-isothiazolyl, 3-, 4- or 5-isoxazolyl, 2-, 4- or 5-imidazolyl, 3- or 4-pyridazinyl, N-oxide-3- or 4-pyridazinyl, 2-, 4- or 5-pyrimidinyl, 4- or 5-(1,2,3-thiadiazolyl), 3- or 5-(1,2,4-thiadiazolyl), 2- or 5-(1,3,4-thiadiazolyl), 3-or 4-(1,2,5-thiadiazolyl), 4- or 5-(1,2,3-oxadiazolyl), 3- or 5-(1,2,4-oxadiazolyl), 1,3,4-oxadiazolyl, 1,2,5-oxadiazolyl, 1,2,3- or 1,2,4-triazolyl, 1H- or 2H-tetrazolyl, pyrido[2,3-d]pyrimidinyl and triazo [2,3-a]pyrimidinyl and the like. Specific examples of a heterocycle in a heterocyclic methyl group for $R^3$ include a 1-pyridyl group, N-methylpyrrolidinium group, N-methyltetrahydroisoindolinium group and 3-thiazolidinium group.

These heterocyclic thiomethyl groups and heterocyclic methyl groups may have been substituted; examples of substituents include a hydroxyl group, an oxo group, a lower alkyl group (the same as above) and —$(CH_2)_xR^a$ (wherein $R^a$ represents a hydroxyl group, a methoxy group, a carbamoyl group, a carboxyl group, a dimethylamino group, a sulfonic acid group, any of the heterocycles described above, or the like; and x represents the integer of 0 to 2). They may also be of the pyridinium type having a methyl group or a carboxymethyl group at the nitrogen in the heterocycle, and may also contain singly, or in combination, groups, such as —$(CH_2)_{2-3}$, which cooperate with the heterocycle to form a condensed ring.

Desirable heterocyclic groups for the heterocyclic thiomethyl group include a 1-methyl-1H-tetrazol-5-yl group, 1-carboxymethyl-1H-tetrazol-5-yl group, 1-(2-hydroxyethyl)-1H-tetrazol-5-yl group, 1-(2-dimethylaminoethyl)-1H-tetrazol-5-yl group, 1-sulfomethyl-1H-tetrazol-5-yl group, 1H-1,2,3-triazol-5-yl group, 5-carboxymethyl-4-methylthiazol-2-yl group, 4-carboxy-3-hydroxyisothiazol-5-yl group, 1,2,3-thiadiazol-5-yl group, 1,2,4-thiadiazol-5-yl group, 1,3,4-thiadiazol-2-yl group, 5-methyl-1,3,4-thiadiazol-2-yl group, N-methyl pyridinium-2-yl group, N-carboxymethyl-pyridinium-4-yl group, 2-carboxy-7-methyl-S-triazolo[2,3-a]pyrimidin- 5-yl group, N-carboxymethyl-cyclopenteno-[b]-pyridinium-4-yl group and 2,5-dihydro-6-hydroxy-2-methyl-5-oxo-1,2,4-triazin-3-yl group. Particularly preferable heterocyclic groups are a 1,2,3-thiadiazol-5-yl group, 1,2,4-thiadiazol-5-yl group, 1,3,4-thiadiazol-2-yl group, 5-methyl-1,3,4-thiadiazol-2-yl group, N-methylpyridinium-2-yl group and N-carboxymethylpyridinium-4-yl group.

Desirable heterocyclic groups for the heterocyclic methyl group include pyridinium, 4-carbamoyl-pyridinium, 4-(2-carbamoylethyl)pyridinium, 4-(2-sulfoethyl)pyridinium, cyclopenteno-[b]-pyridinium, 4-(2-oxazolyl)pyridinium, 4-(5-oxazolyl)pyridinium, 5-methyl-1H-tetrazol-2-yl, 3-allyl-1-imidazolinium, pyrazolo[1,5-a]pyridinium-3-yl and N-methyl-5,6-dihydroxyisoindolinium, 1-methyl pyrrolidinium. Particularly preferable heterocyclic groups are pyridinium and 4-(2-carbamoylethyl)pyridinium.

The ester residue for $R^4$ means a group capable of forming an ester in cooperation with the 4-position carboxyl group in general formula (I): its examples include an alkyl group (e.g. those having 1 to 4 carbon atoms, such as methyl, ethyl, n-propyl, isopropyl, n-butyl and t-butyl), 1-alkanoyloxyalkyl, 1-alkoxycarbonyloxyalkyl, phthalidyl, 5-methyl-2-oxo-1,3-dioxolen-4-ylmethyl and also protective groups for the carboxyl group as described below.

The number of carbon atoms of the alkanoyl moiety in the 1-alkanoyloxyalkyl group is 2 to 10, preferably 2 to 7, and the number of carbon atoms of the alkyl moiety is 1 to 3, preferably 1 or 2. Examples of such groups include acetoxy-methyl, propionyloxymethyl, n-butyryloxymethyl, isobutyryloxymethyl, pivaloyloxymethyl, n-valeryloxymethyl, 2-methylbutyryloxymethyl, isovaleryloxymethyl, n-hexanoyloxymethyl, 3-methylvaleryloxymethyl, neohexanoyloxymethyl, 2-methylhexanoyloxymethyl, 2,2-dimethylbutyryloxymethyl, diethylacetoxymethyl, dipropylacetoxymethyl, 2,2-dimethylvaleryloxymethyl, neoheptanoyloxymethyl, cyclohexanecarbonyloxymethyl, cyclohexylacetoxymethyl, 1-acetoxyethyl, 1-propionyloxyethyl, 1-n-butyryloxyethyl, 1-isobutyryloxyethyl, 1-n-valeryloxyethyl, 1-pivaloyloxyethyl, 1-isovaleryloxyethyl, 1-n-hexanolyloxyethyl and 1-cyclohexanecarbonyloxyethyl.

The number of carbon atoms of the alkoxy moiety in the alkoxycarbonyloxyalkyl group is preferably 1 to 10, more preferably 1 to 7, and the number of carbon atoms of the alkyl moiety is preferably 1 to 3, more preferably 1 or 2. Examples of such groups include 1-methyoxycarbonyloxyethyl, 1-ethoxycarbonyloxyethyl, 1-n-propoxycarbonyloxyethyl, 1-isopropoxycarbonyloxyethyl, 1-n-butoxycarbonyloxyethyl, 1-tert-butoxycarbonyloxyethyl, 1-pentyloxycarbonyloxyethyl and 1-cyclohexyloxycarbonyloxyethyl.

As examples of preferred esters other than protective groups for the carboxyl group, mention may be made of acetoxymethyl, propionyloxymethyl, n-butyryloxymethyl, isovaleryloxymethyl, pivaloyloxymethyl, 1-acetoxyethyl, 1-propionyloxyethyl, 1-isobutyryloxyethyl, 1-n-valeryloxyethyl, 1-isovaleryloxyethyl, 1-pivaloyloxyethyl, phthalidyl, 1-ethoxycarbonyloxyethyl, 1-cyclohexyloxycarbonyloxyethyl and 5-methyl-2-oxo-1,3-dioxolen-4-ylmethyl.

It is desirable that the compound of general formula (I) be a syn isomer.

Examples of amino-protective groups for $R^1$ and $R^5$ include phthaloyl, formyl, monochloroacetyl, dichloroacetyl, trichloroacetyl, trifluoroacetyl, methoxycarbonyl, ethoxycarbonyl, t-butoxycarbonyl, 2,2,2-trichloroethoxycarbonyl, benzyloxycarbonyl, p-nitrobenzyloxycarbonyl, diphenylmethyloxycarbonyl, methoxymethyloxycarbonyl, trityl and trimethylsilyl.

The cephalosporin compounds (I) of the present invention exhibit optical activities with respect to the configuration of the carbon atom or the atomic group marked with an asterisk (*) in general formula (I). Its optically active compounds occur as the optically active isomer A and optically active isomer B described below. The optically active isomers A and B and racemates are all involved in the present invention.

The optically active isomer A is the optically active isomer of 7-[2-(2-aminothiazol-4-yl)-2-(2-amino-1-ethylethoxyimino)acetamido]-cephalosporanic acid (syn isomer), a compound represented by general formula (I), having a specific rotation of +56°. The optically active isomer B is the optically active isomer of 7-[2-(2-aminothiazol-4-yl)-2-(2-amino-1-ethylethoxyimino)acetamido]-cephalosporanic acid ("syn" isomer), a compound represented by the general formula (I), having a specific rotation of +91°.

The cephalosporin compounds (I) form pharmacologically acceptable salts, preferably acid-addition salts at the amino group thereof. There is no particular limitation to the selection of the acid for the formation of said acid-addition salts, as long as it is a pharmaceutically acceptable acid. Examples of such acids include mineral acids, such as hydrochloric acid, sulfuric acid, phosphoric acid and nitric acid; and organic acids, such as oxalic acid, fumaric acid, maleic acid, citric acid, tartaric acid, methanesulfonic acid and toluenesulfonic acid.

The cephalosporin compounds (I) of the present invention may also form salts at the carboxyl group thereof. Examples of such salts include alkali metal salts (e.g. sodium salt, potassium salt), alkaline earth metal salts (e.g. calcium salt) and organic base salts (e.g. pyridine salt).

The cephalosporin compounds (I) and pharmacologically acceptable addition salts thereof are produced, for instance, by any one of the following methods (1), (2), (3) or (4).

(1) The method in which the 7-aminocephalosporanic acid compound (II) represented by the general formula (II):

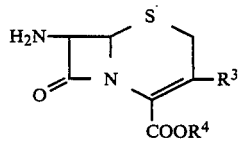
(II)

(wherein $R^3$ and $R^4$ have the same definitions as above) is reacted with the carboxylic acid compound (III) represented by the general formula (III):

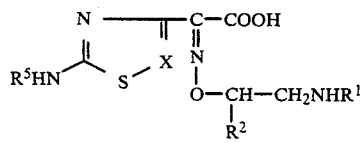
(III)

(wherein $R^1$, $R^2$, $R^5$ and X have the same definitions as above or with its reactive derivative), and the amino-protective group, as necessary, and $R^4$ (in cases where $R^4$ is an ester residue), as necessary, are eliminated.

(2) The method in which the compound (IV) represented by the general formula (IV):

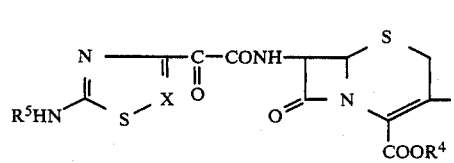
(IV)

(wherein $R^3$, $R^4$, $R^5$ and X have the same definitions as above) is reacted with the hydroxylamine compound (V) represented by the general formula (V):

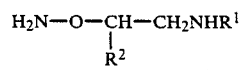
(V)

(wherein $R^1$ and $R^2$ have the same definitions as above), and the amino-protective group, as necessary, and $R^4$ (in cases where $R^4$ is an ester residue), as necessary, are eliminated.

(3) The method in which the compound (VI) represented by the general formula (VI):

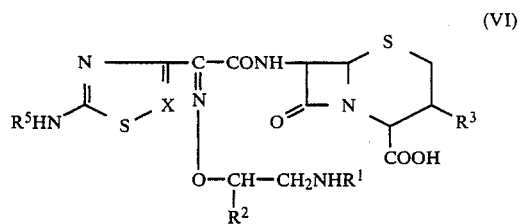
(VI)

(wherein $R^1$, $R^2$, $R^3$, $R^5$ and X have the same definitions as above or its reactive derivative) is reacted with the compound (VII) represented by the general formula (VII):

$$Y-R^4 \quad (VII)$$

(wherein $R^4$ has the same definition as above; and Y represents a carboxyl group or a group which is reactable with a reactive group of a carboxyl group), and the amino-protective group, as necessary, and $R^4$ (in cases where $R^4$ is an ester residue), as necessary, are eliminated.

(4) The method in which a particular compound of the cephalosporin compounds (I), namely, the compound (I-1) represented by the general formula:

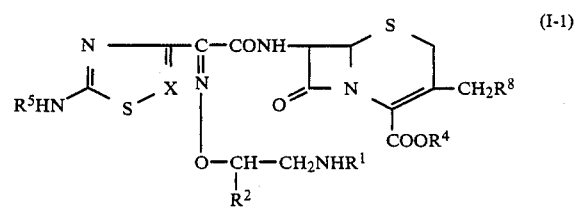
(I-1)

[wherein $R^1$, $R^2$, $R^4$, $R^5$ and X have the same definitions as above; and $R^8$ is a group represented by $-S-R^7$ (wherein $R^7$ represents a heterocyclic group which may have been substituted)] or a nitrogenous heterocyclic compound containing 1 or more nitrogen atoms or sulfur atoms as hetero atoms, is produced by reacting the compound (VIII) represented by the general formula (VIII):

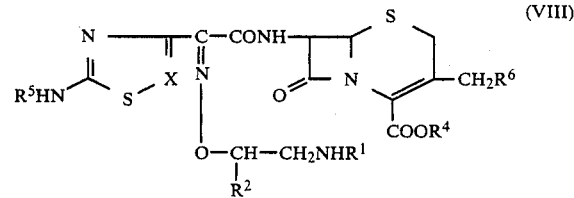
(VIII)

(wherein $R^1$, $R^2$, $R^4$, $R^5$ and X have the same definitions as above; and $R^6$ represents a group which can be substituted by a nucleophilic reagent, such as chloro, bromo, acetoxy, acetoacetoxy, mesyloxy or tosyloxy), with the heterocyclic thiol compound (IX) represented by the formula (IX):

$$R^7-SH \quad (IX)$$

(wherein R⁷ has the same definition as above), or a nitrogenous heterocyclic compound containing 1 or more nitrogen atoms or sulfur atoms as hetero atoms, and the amino-protective group, as necessary, and R⁴ (in cases where R⁴ is an ester residue), as necessary, are eliminated.

As the carboxyl-protective group for R⁴ in general formulae shown above, groups used for the purpose of β-lactam and peptide syntheses are used as appropriate. Specific examples of such groups include t-butyl, t-amyl, benzyl, p-nitrobenzyl, p-methoxybenzyl, benzhydryl, phenyl, p-nitrophenyl, methoxymethyl, ethoxymethyl, benzyloxymethyl, actoxymethyl, methylthiomethyl, trityl, 2,2,2-trichloroethyl, trimethylsilyl, dimethylsilyl, diphenylmethoxybenzenesulfonylmethyl and dimethylaminoethyl.

The acylation in the above production method (1) is achieved by reacting the 7-aminocephalosporanic acid compound (II) normally with a carboxy-reactive derivative of the carboxylic acid compound (III) in a ratio of 1 to 3 moles of the reactive derivative to 1 mole of the compound (II).

With respect to this reaction, examples of salts of the 7-aminocephalosporanic acid compound (II) include hydrochlorides and toluenesulfonates and the like.

Examples of reactive derivatives of the carboxylic acid compound (III) include acid halides, acid anhydrides, active amides and active esters. Preferred examples include acid chlorides, acid bromides, mixed acid anhydrides with acetic acid, pivalic acid, isovaleric acid, trichloroacetic acid, etc., active amides with pyrazole, imidazole, dimethylpyrazole and benzotriazole, active esters, such as p-nitrophenyl ester, 2,4-dinitrophenyl ester, trichlorophenyl ester, 1-hydroxy-1H-2-pyridone ester, N-hydroxysuccinimide ester, N-hydroxyphthalimide ester, and the like.

Furthermore, when the carboxylic acid compound (III) is used in a free acid form in this reaction, it is preferable that the reaction be carried out in the presence of a condensing agent. Examples of preferred condensing agents include carbodiimide compounds, such as N,N-dicyclohexylcarbodiimide, 1-ethyl-3-(3'-dimethylaminopropyl)carbodiimide, N-cyclohexyl-N'-morpholinoethylcarbodiimide and N-cyclohexyl-N'-(4-diethylaminocyclohexyl)carbodiimide; and reagents formed by reaction between an amide compound such as N-methylformamide or N,N-dimethylformamide and a halide such as thionyl chloride, phosphorus oxychloride or phosgene (what are called Vilsmeier reagents).

The acylation reaction for the acid halides and acid anhydrides among the reactive derivatives in this reaction is normally carried out in the presence of an acid condensing agent. Usable acid condensing agents include organic bases such as triethylamine, tributylamine, ethyldiisopropylamine, N,N-dimethylaniline, N-methylmorpholine and pyridine; hydroxides of sodium, potassium or calcium; and carbonates, bicarbonates, etc. of alkali metals and alkaline earth metals.

This reaction is usually carried out in a solvent which does not exert an adverse influence to the reaction. As the solvent, there can be used water, acetone, acetonitrile, dioxane, tetrahydrofuran, methylene chloride, chloroform, dichloroethane and N,N-dimethylformamide or mixed solvents thereof.

Although reaction temperature is not particularly limited, this reaction is carried out usually at −30° to 40° C., and the reaction will complete itself in 30 minutes to 10 hours.

When the compound thus obtained has a protective group for R⁵, R⁴ or R¹, it is subjected to protective group elimination reaction as necessary. Methods which can be chosen according to the type of the protective group for use to eliminate the protective group include decomposition by acid (e.g. hydrochloric acid and trifluoroacetic acid for formyl group, benzhydryl group, t-butoxycarbonyl group, etc.), decomposition by a base (e.g. sodium hydroxide and sodium bicarbonate for dichloroacetyl group, trifluoroacetyl group, etc.), decomposition by phenol (e.g. phenol for p-methoxybenzyl gorup, benzhydryl group, etc.), decomposition by hydrazine (e.g. hydrazine for phthaloyl group, etc.) and catalytic reduction (e.g. palladium-carbon for benzyl group, benzyloxycarbonyl group, etc.). These can be achieved by methods chosen as appropriate from the routine methods used in β-lactam and peptide syntheses.

The compound (III) can be produced by reacting the compound (X) represented by the general formula (X):

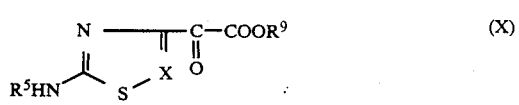

(wherein R⁵ and X have the same definitions as above; R⁹ represents a hydrogen atom or an ester residue) with the hydroxylamine compound (V) or by reacting the compound (XI) represented by the general formula (XI):

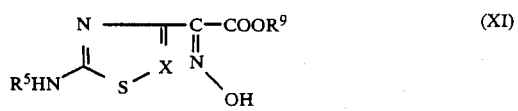

(wherein R⁵, R⁹ and X have the same definitions as above) with the compound (XII) represented by the general formula (XII):

(wherein R¹ and R² have the same definitions as above; W represents a group which can be substituted by a nucleophilic reagent, such as halogen, tosyloxy and mesyloxy), and eliminating R⁹ (in cases where R⁹ is an ester residue) as necessary.

Examples of the ester residue for R⁹ are the same as those for R⁴.

The reaction between the compound (X) and the hydroxylamine compound (V) can be carried out in the same manner as in the above-mentioned reaction between the compound (IV) and the hydroxylamine compound (V), and this reaction generally proceeds more rapidly when the carboxylic acid is in a free form.

The reaction between the compound (XI) and the compound (XII) is carried out in the presence of a base, such as sodium hydride, potassium tert-butoxide, potassium carbonate or sodium carbonate in an organic solvent such as N,N-dimethylformamide, N,N-dimethylacetamide, dimethylsulfoxide, dioxane, tetrahydrofuran or other solvent which does not affect the reaction. Reaction time is usually 30 minutes to 10 and several hours. Although reaction temperature is not particularly limited, the reaction is usually carried out at room temperature to 60° C.

In the above-mentioned production method (2), the reaction between the compound (IV) and the hydroxylamine compound (V) is carried out usually in a solvent which does not adversely affect the reaction such as dimethylformamide, dimethylacetamide, acetonitrile, dioxane, tetrahydrofuran or alcohol, or their mixture with water. Reaction time is usually 30 minutes to 10 and several hours. Although reaction temperature is not particularly limited, the reaction is usually carried out at room temperature to 60° C. The compound (I) having no protective group can be obtained by eliminating the protective group as necessary by the same method as above from the compound thus obtained.

The compound (IV) as the starting material in the above-mentioned production method (2) can be prepared by a known method, i.e. by acylating the 7-aminocephalosporanic acid compound (II) with the compound (X).

A compound of general formula (V) can be produced in accordance with a known method (e.g. Japanese Patent Application laid open No. 149289/1980), i.e. by hydrazinolysis following reaction between N-hydroxylphthalimide and a corresponding active halide in the presence of a base.

Otherwise, a compound of general formula (V) can be obtained in accordance with "Synthesis" (682, 1976), i.e. by reacting the compound (XIII) represented by the general formula (XIII):

(XIII)

wherein $R^1$ and $R^2$ have the same definitions as above, with N-hydroxyphthalimide in the presence of triphenylphosphine and diethyl azodicarboxylate to thereby give the compound (XIV) represented by the general formula (XIV):

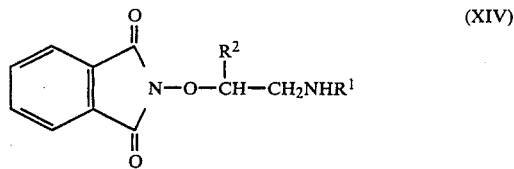

(XIV)

wherein $R^1$ and $R^2$ have the same definitions as above, and decomposing this compound with hydrazine. This process of reacting the compound (XIII) is performed by reacting 1 mole of the compound (XIII) with 1 to 2 moles of triphenylphosphine and diethyl azodicarboxylate. This reaction is carried out normally in an inert solvent such as dioxane, tetrahydrofuran, acetonitrile, methylene chloride, benzene or ether, preferably under non-aqueous conditions. Although reaction temperature is not particularly limited, the reaction is usually carried out at 0° to 30° C., and the reaction will complete itself in 1 to 10 hours. The compound (XIV) thus obtained is subjected to hydrazinolysis by a routine method, whereby the desired compound (V) can be obtained.

In the above-mentioned production method (3), it is preferable that the compound (VI) be employed for this reaction as a reactive derivative thereof (e.g. alkali metal salts such as sodium salt, potassium salt and cesium salt; alkaline earth metal salts such as calcium salt and the like; organic amine salts such as triethylamine salt and pyridine salt).

It is preferable that this reaction be carried out under cooling conditions in order to prevent by-production of a $\Delta^2$-isomer, and this reaction is allowed to proceed easily in the presence of a solvent which does not interfere with the reaction (e.g. dimethylformamide, dimethylacetamide, hexamethylene phosphoric triamide, acetone, acetonitrile).

Examples of a carboxyl-reactive group for Y in general formula (VII) include a hydroxyl group, halogen atom (preferably chlorine atom, bromine atom, iodine atom), sulfonic acid group ($SO_3H$) and sulfonyloxy groups (methanesulfonyloxy group, tosyloxy group, etc.).

Further, it is usually preferable that the reaction between the compound (VIII) having an acetoxy group or acetoacetoxy group for $R^6$ in general formula (VIII) and the heteroxyclic thiol compound (IX) or a nitrogenous heterocyclic compound in the above-mentioned production method (4) be carried out in a polar solvent such as water, phosphate buffer, acetone, acetonitrile, N,N-dimethylformamide, N,N-dimethylacetamide, tetrahydrofuran, dimethylsulfoxide, methanol and ethanol or in a mixed solvent with water.

It is preferable that the reaction be carried out at a nearly neutral pH value.

Although reaction temperature is not particularly limited, it is usually appropriate to carry out the reaction at room temperature to about 70° C. Reaction time varies according to the reaction conditions and the type of the desired 3-position substituent, but it is usually 1 to 7 hours.

In the case of reaction with a nitrogenous heterocyclic compound, such as a pyridine compound, a quinoline compound or pyrazine, it is preferable that the reaction be carried out in the presence of an alkali metal halide such as sodium iodide or potassium iodide.

On the other hand, in the case of the weakly nucleophilic heterocyclic thiol compound (IX), it is preferable that the cephalosporin compounds (I) be produced by reaction with the compound of general formula (VIII) having a halogen atom for $R^6$. Examples of the halogen atom include a chlorine atom, bromine atom and an iodine atom, and an iodine atom is generally preferred because of its reactivity. The compound of general formula (VIII) having an iodine atom for $R^6$ can easily be prepared, in accordance with a known method (e.g. Japanese Patent Application laid open No. 131590/1981), from the above-mentioned compound having an acetoxy group for $R^6$ with its amino group or carboxyl group protected.

It is usually preferable that this reaction be carried out in a solvent such as acetone, dioxane, tetrahydrofuran, ethyl acetate, acetonitrile, dimethylformamide or dimethylacetamide under non-aqueous conditions. The reaction is carried out usually at 0° to 50° C., preferably at 10° to 30° C., and the reaction will complete itself in 1 to 5 hours. From the reactive product thus obtained, the protective group is eliminated by a routine method as necessary, whereby the compound (I-1) of the cephalosporin compounds (I) can be obtained.

The cephalosporin compounds (I) can be converted to pharmacologically acceptable addition salts thereof by a per se known method.

The cephalosporin compounds (I) as obtained by any one of the above methods or pharmacologically acceptable addition salts thereof are isolated from the reaction mixture by a routine method; for example, said compounds or addition salts thereof can be purified by elution with an aqueous organic solvent following adsorption to an adsorptive resin such as Amberlite XAD-2 (Rohm and Haas) or Diaion HP-20 (Mitsubishi Chemical Industries). Also, it is efficient to conduct chromatography with Sephadex LH-20, G-10 (Pharmacia) as necessary.

The cephalosporin compounds (I) according to the present invention or pharmacologically acceptable addition salts thereof are compounds having a unique structure in which a substituent as defined in this invention is present at the α-position carbon atom adjacent to the oxime's oxygen atom and in which no substituent other than an amino group is present at any of the second and following carbon atoms as counted from said oxygen atom, and possess noticeable antibacterial activities on Gram-positive bacteria and Gram-negative bacteria. Said compounds or addition salts thereof exhibit noticeable antibacterial activities even on Pseudomonas aeruginosa, on which known cephalosporin compounds do not exhibit antibacterial activities, and moreover, work well against ordinary Gram-positive bacteria and Gram-negative bacteria. Having a low toxicity and exhibiting a favorable drug disposition, the cephalosporin compounds (I) of the present invention or pharmacologically acceptable addition salts therof can be used as a therapeutic drug for infectious diseases singly or in a pharmaceutical composition.

When used as a pharmaceutical, the compounds (I) of the present invention or pharmacologically acceptable addition salts thereof are administered as a preparation in an appropriate dosage form (e.g. peroral preparations, such as tablets, sugar-coated tablets and capsules; and parenteral preparations, such as injections, suppositories and external preparations) which is prepared by mixing as necessary a therapeutically effective amount of said compound or addition salt thereof with pharmacologically acceptable excipients or additives (e.g. diluents, fillers, emulsifiers, lubricants, flavors, coloring agents).

Although dosage amount of the cephalosporin compounds (I) of the present invention or pharmacologically acceptable addition salts thereof vary according to the symptoms, body weight, age, administration method, and the like, said compounds or addition salts thereof are usually administered to an adult in a dose of 50 mg to 10 g, preferably 200 mg to 5 g daily at a frequency of 1 to several times a day.

The cephalosporin compounds (I) or pharmacologically acceptable addition salts may be used in combination with other antibacterial substances, such as antibacterial agents (e.g. penicillins, aminoglucosides, cephalosporins) or therapeutic drugs for systemic symptoms due to bacterial infection (e.g. antipyretics, analgesics, anti-inflammatories).

Test examples

The minimum inhibitory concentrations (MIC) of some compounds according to this invention were determined. The results are shown in Tables 1 and 2. As the controls, CTX and CAZ, both of which are compounds having a hydrogen atom for $R^2$, and similar compounds having a different oxime moiety were used.

TABLE 1
(Minimum Growth Inhibitory Concentrations (μg/ml))

| | Compound of this invention | | | | | | Control | | | |
|---|---|---|---|---|---|---|---|---|---|---|
| No. | 1 | 2 | 3 | 7 | 10 | | Oxime moiety:* −OCH₂CHNH₂ / CH₃ | Oxime moiety:** −OCH−CHNH₂ / CH₃ CH₃ | | |
| R² | −CH₃ | −C₂H₅ | (cyclopropyl) | −C₂H₅ | −C₂H₅ | H | | | | |
| R³ | −CH₂−S−(thiadiazole) | −CH₂−S−(thiadiazole) | −CH₂−S−(thiadiazole) | −CH₂−O−C(=O)CH₃ | −CH₂−S−(pyridinium-CH₂COOH) | −CH₂−S−(triazole) | R³: −CH₂S−(N-N/S thiadiazole) | R³: −CH₂S−(N-N/S thiadiazole) | | |
| Test bacterium | X | | | | | | | | CTX | CAZ |
| S. aureus 209PJC-1 | CH | 0.39 | 0.39 | 0.39 | 0.78 | 0.78 | 0.78 | 0.78 | 0.78 | 0.78 | 3.13 |
| M. luteus ATCC 9341 | CH | ≦0.025 | ≦0.025 | ≦0.025 | ≦0.025 | ≦0.025 | ≦0.025 | ≦0.025 | ≦0.025 | 0.05 | 0.39 |
| B. subtilis ATCC 6633 | CH | 0.20 | 0.2 | 0.2 | 0.2 | 0.2 | 0.2 | 0.20 | 0.20 | 0.39 | 3.13 |
| E. coli KC-14 | CH | ≦0.025 | 0.05 | 0.1 | ≦0.025 | ≦0.025 | ≦0.025 | ≦0.025 | 0.1 | ≦0.025 | 0.1 |
| K. pneumoniae KC-1 | CH | ≦0.025 | ≦0.025 | ≦0.025 | ≦0.025 | ≦0.025 | ≦0.025 | ≦0.025 | 0.05 | ≦0.025 | 0.05 |
| S. marcescens IFO 3736 | CH | ≦0.025 | 0.05 | 0.1 | 0.05 | ≦0.025 | 0.05 | 0.1 | 0.2 | 0.1 | 0.1 |
| P. aeruginosa No. 12 | CH | 3.13 | 3.13 | 3.13 | 1.56 | 1.56 | 25 | 25 | 6.25 | 25 | 1.56 |
| P. aeruginosa Nc-5 | CH | 3.13 | 3.13 | 3.13 | 1.56 | 1.56 | 25 | 12.5 | 12.5 | 25 | 1.56 |
| P. aeruginosa KY-007 | CH | 3.13 | 3.13 | 3.13 | 3.13 | 3.13 | 25 | 25 | 6.25 | | |
| P. aeruginosa KR-014 | CH | 3.13 | 3.13 | 3.13 | 3.13 | 3.13 | 25 | 12.5 | 12.5 | | |
| P. aeruginosa KR-019 | CH | 3.13 | 3.13 | 6.25 | 6.25 | 6.25 | 25 | 50 | 50 | | |
| P. aeruginosa KR-028 | CH | 3.13 | 3.13 | 3.13 | 3.13 | 3.13 | 25 | 12.5 | 12.5 | | |
| P. aeruginosa KF-042 | CH | 3.13 | 3.13 | 3.13 | 3.13 | 3.13 | 25 | 25 | 6.25 | | |
| P. aeruginosa KF-055 | CH | 6.25 | 6.25 | 6.25 | 12.5 | 12.5 | 50 | 25 | 25 | | |

*7-[2-(2-Aminothiazol-4-yl)-2-(2-aminopropoxyimino)acetamido]-3-(1,3,4-thiadiazol-2-yl)thiomethyl-3-cephem-4-carboxylic acid dihydrochloride (syn isomer)
**7-[2-(2-Aminothiazol-4-yl)-2-(2-amino-1-methylpropoxyimino)acetamido]-3-(1,3,4-thiadiazol-2-yl)thiomethyl-3-cephem-4-carboxylic acid dihydrochloride (syn isomer)

TABLE 2

| | | (Minimum Growth Inhibitory Concentrations μg/ml) | | |
|---|---|---|---|---|
| | | Compound of this invention | | | |
| Test bacterium | No. $R^2$ $R^3$ X | 7 —$C_2H_5$ —$CH_2OCOCH_3$ CH | 15 —$CH_3$ —$CH_2OCOCH_3$ CH | 17 —$CH_3$ —$CH_2OCOCH_3$ CH | 19 —$C_2H_5$ —$CH_2OCOCH_3$ CH |
| S.aureus Smith | | 6.25 | 3.13 | 3.13 | 3.13 |
| S.aureus AR-061 | | 3.13 | 1.56 | 1.56 | 1.56 |
| E.coli NIHJ JC-2 | | 0.10 | 0.05 | ≦0.025 | 0.05 |
| K.pneumoniae NCTC 9632 | | 0.10 | 0.10 | 0.05 | 0.05 |
| P.vulgaris OX-19 | | 0.05 | ≦0.025 | ≦0.025 | ≦0.025 |
| P.mirabilis 1287 | | 0.20 | 0.20 | 0.10 | 0.10 |
| P.aeruginosa No.12 | | 1.56 | 3.13 | 3.13 | 0.78 |
| P.aeruginosa E-2 | | 3.13 | 3.13 | 3.13 | 1.56 |

EXAMPLE 1

7-[2-(2-Aminothiazol-4-yl)-2-(2-amino-1-methylethoxyimino)acetamido]-3-(1,3,4-thiadiazol-2-yl)thiomethyl-3-cephem-4-carboxylic acid dihydrochloride (syn isomer)

(1) To 20 g of 1-amino-2-propanol, 69.7 g of di-t-butyl-dicarbonate is added in portions under cooling conditions and this is followed by 1 hour of agitation at room temperature, whereafter 1 l of ethyl acetate is added, and the mixture is washed with water. The organic layer is dried with anhydrous Glauber's salt, after which it is concentrated under reduced pressure. The residue is subjected to silica gel column chromatography and eluted with chloroform-methanol to give 46 g of 1-t-butoxycarbonylamino-2-propanol.

IR (Neat, $cm^{-1}$); 3350, 1690, 1520

NMR ($CDCl_3$, δppm); 1.18 (d, J=7 Hz, 3H, —$CH_3$) 1.46 (s, 9H, Boc—), 2.3∼2.65 (br, 1H, —OH), 2.9∼3.30 (br, 2H, —$CH_2$—), 3.7∼4.1

(m, 1H, —OĊH—), 4.7∼5.2 (br, 1H, —CONH—)

(2) 10 g of the product obtained in (1) and 28.4 g of carbon tetrabromide are dissolved in 50 ml of acetonitrile, and 17.9 g of triphenylphosphine is added in portions at room temperature over a period of 1 hour. After 1 hour of agitation, the mixture is extracted with 500 ml of benzene and 300 ml of water. The organic layer is washed with a sodium chloride solution and dried with anhydrous Glauber's salt, after which it is concentrated under reduced pressure. The residue is subjected to silica gel column chromatography and eluted with benzene-ethyl acetate. The desired fraction is concentrated to give 13.1 g of 1-(t-butoxycarbonylamino)-2-bromopropane.

IR (Neat, $cm^{-1}$); 3340, 1700, 1510

NMR ($CDCl_3$, δppm); 1.48 (s, 9H, Boc—), 1.67 (d, J=7 Hz, 3H, —$CH_3$), 3.42 (m, 2H, —$CH_2$—), 3.85∼4.50 (m, 1H, —CH<), 4.5∼5.3 (br, 1H, —CONH—)

(3) 8.9 g of N-hydroxyphthalimide is dissolved in 100 ml of dimethylformamide, and 2.4 g of sodium hydride is added. After 30 minutes of agitation, 13 g of the product obtained in (2) is added, and this is followed by 1 hour of agitation at 120° C. 1 of ethyl acetate is added, and this mixture is washed with water and a sodium chloride solution, after which it is dried with anhydrous Glauber's salt. After evaporation of the solvent under reduced pressure, the residue is subjected to silica gel column chromatography and eluted with benzene-ethyl acetate, whereafter 4.09 g of 1-t-butoxycarbonylamino-2-phthalimido-oxy-propane is obtained from the desired fraction.

IR (Neat, $cm^{-1}$); 3420, 1730

NMR ($CDCl_3$, δppm); 1.35 (d, J=7 Hz, 3H, —$CH_3$), 1.48 (s, 9H, —Boc), 3.31 (m, 2H, —$CH_2$—), 4.05∼4.55 (m, 1H, —OCH<), 5.45∼5.85 (br, 1H, —CONH—), 7.34 (s, 4H, phenyl)

(4) 2.4 g of the product obtained in (3) is dissolved in 50 ml of methylene chloride. To this solution, 750 mg of hydrazine hydrate is added at room temperature, and this is followed by 1 hour of agitation. The precipitate is removed by filtration, and the solvent is evaporated under reduced pressure. 150 ml of 70% aqueous tetrahydrofuran solution is added, and 1.77 g of 2-(2-formamidothiazol-4-yl)glyoxylic acid is then added, and this is followed by 1 hour of agitation at pH 5. The tetrahydrofuran is evaporated under reduced pressure, and the residue is extracted with 200 ml of ethyl acetate at pH 3. The extract is washed with a sodium chloride solution and dried with anhydrous Glauber's salt, whereafter 1.4 ml of dicyclohexylamine is added, and the separating crystal is collected by filtration and dried.

The crystal is recrystallized with 60 ml of isopropyl alcohol and is added into 200 ml of ethyl acetate and washed with 200 ml of 10% citric acid. The organic layer is washed with a sodium chloride solution, dried with anhydrous Glauber's salt, and concentrated under reduced pressure to give 1.29 g of 2-(2-formamidothiazol-4-yl)-2-(2-t-butoxycarbonylamino-1-methylethoxyimino)acetic acid (syn isomer).

IR (Nujol, $cm^{-1}$); 1690, 1610

NMR (DMSO-$d_6$, δppm); 1.15 (d, J=7 Hz, 3H, —$CH_3$), 1.38 (s, 9H, Boc—), 3.12 (m, 2H, —$CH_2$—), 3.9∼4.4 (m, 1H, —OCH<), 6.45∼6.85 (br, 1H, —NH—), 7.43 (s, 1H, thiazole 5-position —H), 8.45 (s, 1H, —CHO), 10.1~11.5 (br, 1H, —CO₂H), 12.6 (s, 1H, —NH—)

(5) 1.34 g of the product obtained in (4) and 1.49 g of benzhydryl 7-amino-3-(1,3,4-thiadiazol-2-yl)thiomethyl-3-cephem-4-carboxylate are dissolved in 50 ml of dry methylene chloride. To this solution, 0.79 ml of pyridine and 0.61 ml of phosphorus oxychloride are added at −10° C., and this is followed by 90 minutes of agitation. 500 ml of ethyl acetate is added, and this mixture is washed with sequential addition of 10% citric acid and a sodium chloride solution, and dried with anhydrous Glauber's salt. The solvent is evaporated under reduced pressure. The residue is solidified with isopropyl ether, subjected to silica gel column chromatography, and eluted with chloroform-methanol, whereafter the desired fraction is concentrated to give 1.21 g of benzhydryl 7-[2-(2-formamidothiazol-4-yl)-2-(2-t-butoxycarbonylamino-1-methylethoxyimino)acetamido]-3-(1,3,4-thiadiazol-2-yl)thiomethyl-3-cephem-carboxylate (syn isomer).

IR (Nujol, cm⁻¹); 1780, 1680

NMR (DMSO-d₆, δppm); 1.20 (d, J=7 Hz, 3H, —CH₃), 1.32 (s, 9H, Boc—), 2.9~3.0 (m, 2H, —CH₂—), 3.5~4.9 (m, 2H, 2-position —H₂), 4.0~4.5 (m, 3H, 3-position —CH₂—, —OCH<), 5.21 (d, J=5 Hz, 1H, 6-position —H), 5.80 (d×d, J=5 Hz, 8 Hz, 1H, 7-position —H), 6.4~6.9 (br, 1H, —NH—), 6.89 (s, 1H, —CH<), 7.0~7.7 (m, 11H, thiazole 5-position —H, phenyl), 8.45 (s, 1H, —CHO), 9.44 (s, 1H, thiadiazole 5-position —H), 9.52 (d, J=8 Hz, 1H, —CONH—), 12.57 (s, 1H, —NH—)

(6) To 1.1 g of the product obtained in (5), 3.3 g of phenol is added, and this is followed by 4 hours of agitation at 45° C. This mixture is extracted with 90 ml of ethyl acetate and 90 ml of 5% aqueous sodium bicarbonate. The aqueous layer is acidized with 10% citric acid and extracted twice with 50 ml of ethyl acetate. The organic layer is washed with a sodium chloride solution, after which it is dried with anhydrous Glauber's salt. The dried organic layer is then concentrated under reduced pressure, solidified with isopropyl ether, and dissolved in 5.7 ml of methanol. To this solution, 0.37 ml of concentrated hydrochloric acid is added, and this is followed by 2 hours of agitation. This mixture is poured to 60 ml of ether, and the separating solid is collected by filtration. To this solid, 5.62 ml of 3.3 v/v% concentrated hydrochloric acid-formic acid is added while cooling with ice, and this is followed by 20 minutes of agitation. This mixture is poured to 50 ml of ether. The separating solid is collected by filtration and dissolved in a small amount of methanol. This solution is again poured into 50 ml of ether, whereafter the separating substance is collected by filtration to give 440 mg of the subject compound.

IR (Nujol, cm⁻¹); 1775, 1710, 1680, 1625

NMR (DMSO-d₆, δppm); 1.34 (d, J=7 Hz, 3H, —CH₃), 2.9~3.5 (m, 2H, —CH₂), 3.6~3.9 (br, 2H, 2-position —H₂), 4.0~4.8 (m, 3H, —CH<, 3-position —CH₂—), 5.15 (d, J=5 Hz, 6-position —H), 5.81 (d×d, J=5 Hz, 8 Hz, 1H, 7-position —H), 6.99 (s, 1H, thiazole 5-position —H), 7.9~9.5 (br, 7H, —NH₃⁺×2, —CO₂H), 9.52 (s, 1H, thiadiazole 5-position —H), 9.78 (d, J=8 Hz, 1H, —CONH—)

EXAMPLE 2

7-[2-(2-Aminothiazol-4-yl)-2-(2-amino-1-ethylethoxyimino)acetamido]-3-(1,3,4-thiadiazol-2-yl)thiomethyl-3-cephem-4-carboxylic acid dihydrochloride (syn isomer)

(1) 5 g of 1-amino-2-butanol and 12.2 g of di-t-butyldicarbonate are treated in the same manner as in Example 1 (1) to give 10 g of 1-t-butoxycarbonylamino-2-butanol. This product is dissolved in 200 ml of dry tetrahydrofuran, and 8.62 g of N-hydroxyphthalimide, 16.63 g of triphenylphosphine and 9.95 ml of diethyl azodicarboxylate are added at room temperature. After 3 hours of agitation, the solvent is evaporated under reduced pressure. The residue is subjected to silica gel column chromatography and eluted with benzene-ethyl acetate, whereafter the desired fraction is concentrated to give 6.3 g of 1-(t-butoxycarbonylamino)-2-phthalimido-oxy-butane.

IR (Nujol, cm⁻¹); 3420, 1785, 1730, 1695, 1510

NMR (CDCl₃, δppm); 1.10 (t, J=7 Hz, 3H, —CH₃), 1.4~2.2 (m, 2H, —CH₂—), 1.46 (s, 9H, Boc—), 3.25~3.58 (m, 2H, —CH₂—), 3.9~4.4 (m, 1H, —CH<), 5.45~5.95 (br, 1H, —NH—), 7.78 (s, 4H, phenyl)

(2) A mixture of 6.2 g of the product obtained in (1), 2.58 ml of hydrazine hydrate and 120 ml of methylene chloride is stirred at room temperature for 30 minutes. The separating insoluble substance is removed by filtration and the solvent is evaporated under reduced pressure. The resulting residue is dissolved in 320 ml of 70% aqueous tetrahydrofuran solution. To this solution, 3.73 g of 2-(2-formamidothiazol-4-yl)glyoxylic acid is added, and this is followed by 90 minutes of agitation at pH 5, whereafter the same procedure as in Example 1 (4) is followed to give 3.5 g of 2-(2-formamidothiazol-4-yl)-2-(2-t-butoxycarbonylamino-1-ethylethoxyimino)acetic acid (syn isomer).

IR (Nujol, cm⁻¹); 1695, 1550

NMR (DMSO-d₆, δppm); 0.91 (t, J=7 Hz, 3H, —CH₃), 1.38 (s, 9H, Boc—), 1.2~2.2 (m, 2H, —CH₂—), 2.9~3.4 (m, 2H, —CH₂—), 3.8~4.4 (m, 1H, —CH<), 6.4~6.9 (br, 1H, —NH—), 7.50 (s, 1H, thiazole 5-position —H), 8.50 (s, 1H, —CHO), 12.0~13.0 (br, 2H, —CO₂H, —NH—)

(3) 2.04 g of the product obtained in (2) and 1.91 g of benzhydryl 7-amino-3-(1,3,4-thiadiazol-2-yl)thiomethyl-3-cephem-4-carboxylate are dissolved in 80 ml of dry methylene chloride. To this solution, 1.12 ml of pyridine and 0.86 ml of phosphorus oxychloride are added at −12° C., and this is followed by 2 hours of agitation at −15° C., whereafter the reaction mixture is treated in the same manner as in Example 1 (5) to give 2.2 g of benzhydryl 7-[2-(2-formamidethiazol-4-yl)-2-(2-t-butoxycarbonylamino-1-ethylethoxyimino)acetamido]-3-(1,3,4-thiadiazol-2-yl)thiomethyl-3-cephem-4-carboxylate (syn isomer).

(4) To 1.98 g of the product obtained in (3), 5.82 g of phenol is added, and this is followed by 4 hours of agtation at 45° C. 50 ml of ethyl acetate is added, and this mixture is extracted twice with 200-ml and 100-ml portions of 5% aqueous sodium bicarbonate. The aqueous layers are combined together and washed with ethyl acetate, whereafter this aqueous layer is acidified with 10% citric acid and extracted twice with 300-ml and 150-ml portions of ethyl acetate. The ethyl acetate layers are combined together, washed with a sodium chloride solution, and dried with anhydrous Glauber's salt. This mixture is then concentrated under reduced pressure and solidified with 200 ml of isopropyl ether to give 1.1 g of 7-[2-(2-formamidothiazol-4-yl)-2-(2-t-butoxycarbonylamino-1-ethylethoxyimino)acetamido]-3-(1,3,4-thiadiazol-2-yl)thiomethyl-3-cephem-4-carboxylic acid (syn isomer)

IR (Nujol, cm⁻¹); 1780, 1690, 1540

NMR (DMSO-d₆, δppm); 0.97 (t, J=7 Hz, 3H, —CH₃), 0.9~2.2 (m, 2H, —CH₂—), 1.34 (s, 9H, Boc—), 2.9~3.5 (m, 2H, —CH₂—), 3.5~3.9 (br, 2H, 2-position —H₂), 3.8~4.9 (m, 3H, 3-position —CH₂, —CH<), 5.16 (d, J=5 Hz, 1H, 6-position —H), 5.84 (d×d, J=5 Hz, 8 Hz, 1H, 7-position —H), 6.4~7.0 (br, 1H, —NH—), 7.34, 7.36 (s, 1H, thiadiazole 5-position —H), 8.47 (s, 1H, —CHO), 9.46 (d, J=8 Hz, 1H, —CONH—), 9.50 (s, 1H, thiadiazole 5-position —H), 12.58 (s, 1H, —NH—)

(5) 1.05 g of the product obtained in (4) is dissolved in 10.5 ml of methanol. To this solution, 0.63 ml of concentrated hydrochloric acid is added at room temperature, and this is followed by 2 hours of agitation. This mixture is poured into 100 ml of diethyl ether and the separating substance is collected by filtration. 5 ml of a 6 v/v% hydrochloric acid-formic acid solution is added, and this mixture, after 20 minutes of agitation, is poured into 100 ml of diethyl ether. The separating substance is collected by filtration and dissolved in a small amount of methanol. This solution is poured into 100 ml of diethyl ether to give 872 mg of the subject compound.

IR (Nujol, cm⁻¹); 1770, 1670, 1625

NMR (DMSO-d₆, δppm); 1.00 (t, J=7 Hz, 3H, —CH₃), 1.2~2.3 (m, 2H, —CH₂—), 2.8~3.6 (m, 2H, —CH₂—), 3.5~4.0 (br, 2H, 2-position —H₂), 4.04~5.0

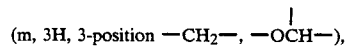

(m, 3H, 3-position —CH₂—, —OCH—), 5.16 (d, J=5 Hz, 1H, 6-position —H), 5.84 (d×d, J=5 Hz, 8 Hz, 1H, 7-position —H), 7.02 (s, 1H, thiazole 5-position —H), 7.6~11.4 (m, 8H, —NH₃⁺×2, —CO₂H, —CONH—), 9.54 (s, 1H, thiadiazole 5-position —H)

EXAMPLE 3

7-[2-(2-Aminothiazol-4-yl)-2-(2-amino-1-cyclopropylethoxyimino)acetamido]-3-(1,3,4-thiadiazol-2-yl)thiomethyl-3-cephem-4-carboxylic acid dihydrochloride (syn isomer)

(1) 2.7 g of 2-amino-1-cyclopropylethanol is dissolved in 20 ml of tetrahydrofuran. To this solution, 6.05 g of di-t-butyl-di-carbonate is added, and this is followed by 20 minutes of agitation. The solvent is evaporated under reduced pressure, and the residue is subjected to silica gel column chromatography and eluted with hexane-ethyl acetate, whereafter the desired fraction is concentrated to give 1.84 g of 2-t-butoxycarbonylamino-1-cyclopropylethanol.

NMR (CDCl₃, δppm); 0.15~1.10 (m, 5H, cyclopropyl), 1.46 (s, 9H, —Boc), 2.54 (brs, 1H, —OH), 2.80~3.70

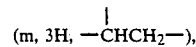

(m, 3H, —CHCH₂—), 5.00 (br, 1H, —NH—)

(2) 1.8 g of the product obtained in (1) is dissolved in 36 ml of dry teterahydrofuran, and 1.61 g of N-hydroxyphthalimide, 3.52 g of triphenylphosphine and 2.1 ml of diethyl azodicarboxylate are added at room temperature. After 1 hour of agitation, this mixture is concentrated under reduced pressure, whereafter benzene is added and the insoluble substance is removed by filtration. The filtrate is concentrated under reduced pressure, after which it is subjected to silica gel column chromatography and eluted with benzene-ethyl acetate, whereafter the desired fraction is concentrated to give 1.69 g of 2-t-butoxycarbonylamino-1-cyclopropyl-1-phthalimido-oxy-ethane.

IR (Neat, cm⁻¹); 3400, 1780, 1730, 1500

NMR (CDCl₃, δppm); 0.15~1.5 (m, 5H, cyclopropyl), 1.46 (s, 9H, Boc—), 3.30~3.75 (m, 3H, >CHCH₂—), 5.55 (br, 1H, —NH—), 7.78 (s, 4H, phenyl)

(3) 1.75 g of the product obtained in (2) is dissolved in 35 ml of methylene chloride. To this solution, 0.74 ml of hydrazine hydrate is added at room temperature and this is followed by 30 minutes of agitation. After removing the separating insoluble substance, the mixture is concentrated under reduced pressure to give 1.07 g of 1-aminoxy-1-cyclopropyl-2-t-butoxycarbonylaminoethane.

IR (Neat, cm⁻¹); 3320, 1700, 1510

NMR (CDCl₃, δppm); 0.1~1.0 (m, 5H, cyclopropyl), 1.45 (s, 9H, Boc—), 2.65~3.8 (m, 3H, >CHCH₂—), 5.0 (br, 1H, —NH—), 5.38 (br, 2H, —NH₂)

(4) 0.97 g of 2-(2-formamidothiazol-4-yl)glyoxylic acid is added to 90 ml of 70% aqueous tetrahydrofuran solution. While stirring this mixture, 1.05 g of the product obtained in (3) is added thereto, and reaction is carried out at room temperature for 1 hour. After evaporation of tetrahydrofuran under reduced pressure, the residue is acidized to pH 3 with 10% citric acid and extracted twice with 100-ml and 50-ml portions of ethyl acetate. The organic layers are combined together, washed with a sodium chloride solution and dried with anhydrous Glauber's salt. This mixture is then concentrated to 25 ml. To this concentrate, 1 ml of dicyclohexylamine is added and this mixture is cooled for 30 minutes. The separating crystal is collected and recrystallized from isopropyl alcohol. This crystal is added to 150 ml of ethyl acetate, washed with sequential addition of 10% citric acid and a sodium chloride solution and dried with anhydrous Glauber's salt. The dried mixture is concentrated under reduced pressure to give 1.28 g of 2-(2-formamidothiazol-4-yl)-2-(2-t-butoxycarbonylamino-1-cyclopropylethoxyimino)acetic acid (syn isomer).

IR (Nujol, cm⁻¹); 1770, 1550

NMR (DMSO-d₆, δppm); 0.1~1.6 (m, 5H, cyclopropyl), 1.4 (s, 9H, Boc—), 2.6~3.7 (m, 3H, >CHCH₂—), 6.64 (br, 1H, —NH—), 7.48 (s, 1H, thiazole 5-position —H), 8.48 (s, 1H, —CHO), 11.6~13.6 (br, 2H, —CO₂H, —NH—)

(5) 1.26 g of the product obtained in (4) and 1.14 g of benzhydryl 7-amino-3-(1,3,4-thiadiazol-2-yl)thiomethyl-3-cephem-4-carboxylate are dissolved in 50 ml of dry methylene chloride. To this solution, 0.67 ml of pyridine and 0.51 ml of phosphorus oxychloride are added at −12° C., and this is followed by 2 hours of agitation at the same temperature. 200 ml of ethyl acetate is added, and this mixture is washed with 10% citric acid and a sodium chloride solution, and dried with anhydrous Glauber's salt. The dried mixture is concentrated under reduced pressure and added to 100 ml of isopropyl ether. The separating substance is collected by filtration, subjected to silica gel column chromatography, and eluted with chloroform-methanol, whereafter 1.34 g of benzhydryl 7-[2-(2-formamidothiazol-4-yl)-2-(2-t-butoxycarbonylamino-1-cyclopropylethoxyimino)acetamido]-3-(1,3,4-thiadiazol-2-yl)thiomethyl-3-cephem-4-carboxylate (syn isomer) is obtained from the desired fraction.

IR (Nujol, cm$^{-1}$); 1780, 1690, 1540

NMR (DMSO-d$_6$, δppm); 0.1~1.6 (m, 5H, cyclopropyl), 1.34 (s, 9H, Boc—), 2.8~3.5 (m, 2H, —CH$_2$—), 3.74 (br, 2H, 2-position —H$_2$), 3.8~4.8

(m, 3H, 3-position —CH$_2$—, —OCH—), 5.24 (d, J=5 Hz, 1H, 6-position —H), 5.98 (d×d, J=5 Hz, 8 Hz, 7-position —H), 6.74 (br, 1H, —NH—), 6.92 (s, 1H, —CH<), 7.0~7.8 (m, 11H, phenyl×2, thiazole 5-position —H), 8.47 (s, 1H, —CHO), 9.44 (s, 1H, thiadiazole 5-position —H), 9.52 (d, J=8 Hz, 1H, —CONH—), 12.56 (br, 1H, —NH—)

(6) 0.88 g of the product obtained in (5) is added to 2.55 g of phenol, and this is followed by 5 hours of agitation at 45° C. 20 ml of ethyl acetate is added and this mixture is extracted twice with 100-ml and 50-ml portions of 5% aqueous sodium bicarbonate. The aqueous layers are combined together and washed with ethyl acetate, whereafter this mixture is acidified with citric acid and extracted twice with 150-ml and 80-ml portions of ethyl acetate. The ethyl acetate layers are combined together, washed with a sodium chloride solution and dried with anhydrous Glauber's salt. After concentration under reduced pressure, the dried mixture is solidified with isopropyl ethyl and dissolved in 4.8 ml of methanol. To this solution, 0.3 ml of concentrated hydrochloric acid is added at room temperature and this is followed by 2 hours of agitation. This mixture is then poured into 50 ml of diethyl ether and the separating solid is collected by filtration. This solid, after being dried, is dissolved in 2.34 ml of a 6 v/v% concentrated hydrochloric acid-formic acid solution, and this is followed by 20 minutes of agitation. This solution is poured into 50 ml of diethyl ether and the separating substance is collected by filtration, whereby 276 mg of the subject compound is obtained.

IR (Nujol, cm$^{-1}$); 1770, 1670, 1620, 1540

NMR (DMSO-d$_6$, δppm); 0.1~1.6 (m, 5H, cyclopropyl), 2.8~3.7 (m, 2H, —CH$_2$—), 3.74 (br, 2H, 2-position —H$_2$), 3.7~4.9 (m, 3H, 3-position —CH$_2$—, —OCH<), 5.18 (d, J=5 Hz, 1H, 6-position —H), 5.80 (d×d, J=5 Hz, 8 Hz, 1H, 7-position —H), 7.00 (s, 1H, thiazole 5-position —H), 7.7~11.0 (m, 8H, —NH$_3$+×2, —CO$_2$H, —CONH—), 9.54 (s, 1H, thiadiazole 5-position —H)

EXAMPLE 4

7-[2-(2-Aminothiazol-4-yl)-2-(2-amino-1-ethylethoxyimino)acetamido]-3-(1,3,4-thiadiazol-2-yl)thiomethyl-3-cephem-4-carboxylic acid dihydrochloride (syn isomer)

(1) 10 g of 1-amino-2-butanol is dissolved in 20 ml of teterahydrofuran. To this solution, 24.5 g of di-t-butyldicarbonate is added, and this is followed by 30 minutes of agitation, whereafter this mixture is concentrated under reduced pressure to give 21.2 g of 1-t-butoxycarbonylamino-2-butanol.

IR (Neat, cm$^{-1}$); 3350, 1695, 1520

NMR (CDCl$_3$, δppm); 0.97 (t, J=7 Hz, 3H, —CH$_3$), 1.1~1.9 (m, 2H, —CH$_2$—), 1.46 (s, 9H, Boc—), 2.9~3.4 (m, 3H, —CH$_2$—, —OH), 3.2~3.85 (br, 1H, —OCH<), 4.9~5.4 (br, 1H, —NH—)

(2) 10.7 g of the product obtained in (1) is dissolved in dry acetonitrile. To this solution, 28.07 g of carbon tetrabromide is added and 17.76 g of triphenylphosphine is added in portions at 8° C. After 1 hour of agitation at room temperature, aectonitrile is evaporated and the residue is extracted with 500 ml of benzene and 300 ml of water. The insoluble substance is removed by filtration, and the benzene layer is washed with a sodium chloride solution and dried with anhydrous Glauber's salt. After evaporation of the solvent, the residue is subjected to silica gel column chromatography and eluted with benzene-ethyl acetate to give 28.2 g of 1-bromo-2-t-butoxycarbonylaminobutane.

NMR (CDCl$_3$, δppm); 1.07 (t, J=7 Hz, 3H, —CH$_3$), 1.47 (s, 9H, Boc—), 1.5~2.2 (m, 2H, —CH$_2$—), 3.2~3.75 (m, 2H, —CH$_2$—), 3.75~4.28 (m, 1H, —CH<), 4.6~5.2 (br, 1H, —NH—)

(3) 743 mg of N-hydroxyphthalimide is dissolved in 8 ml of dry dimethylformamide. To this solution, 201 mg of sodium hydride is added and this is followed by 30 minutes of agitation. 1.0 g of the product obtained in (2) is added, and this mixture is agitated for 1 hour at 120° C. 80 ml of ethyl acetate is added, and this mixture is washed with water and a sodium chloride solution, after which it is dried with anhydrous Glauber's salt. After evaporation of the solvent under reduced pressure, the residue is subjected to silica gel column chromatography and eluted with benzene-ethyl acetate to give 198 mg of 1-t-butoxycarbonylamino-2-phthalimido-oxybutane.

IR (Nujol, cm$^{-1}$); 3420, 1785, 1730, 1695

NMR (CDCl$_3$, δppm); 1.10 (t, J=7 Hz, 3H, —CH$_3$), 1.4~2.2 (m, 2H, —CH$_2$—), 1.46 (s, 9H, Boc—), 3.25~3.58 (m, 2H, —CH$_2$—), 3.9~4.4 (m, 1H, —OCH<), 5.45~5.95 (br, 1H, —NH—) 7.78 (s, 4H, phenyl)

(4) 160 mg of the product obtained in (3) is treated in the same manners as in Example 2 (2) through (5) to give 51 mg of the subject compound.

IR (Nujol, cm$^{-1}$); 1770, 1670, 1625

NMR (DMSO-d$_6$, δppm); 1.00 (t, J=7 Hz, 3H, —CH$_3$), 1.2~2.3 (m, 2H, —CH$_2$—), 2.8~3.6 (m, 2H, —CH$_2$—), 3.5~4.0 (br, 2H, 2-position —CH$_2$), 4.04~5.0 (m, 3H, 3-position —CH$_2$—, —OCH<), 5.16 (d, J=5 Hz, 1H, 6-position —H), 5.84 (d×d, J=5 Hz, 8 Hz, 1H, 7-position —H), 7.02 (s, 1H, thiazole 5-position —H), 7.6—11.4 (m, 8H, —NH$_3$+×2, —CO$_2$H, —CONH—), 9.54 (s, 1H, thiadiazole 5-position —H)

EXAMPLE 5

7-[2-(2-Aminothiazol-4-yl)-2-((S)-2-amino-1-methylethoxyimino)acetamido]-3-(1,3,4-thiadiazol-2-yl)thiomethyl-3-cephem-4-caroxylic aicd dihydrochloride (syn isomer)

(1) 2.0 g of R(—)-1-amino-2-propanol is subjected to the procedure of Example 2 to give 367 mg of the subject compound.

IR (Nujol, cm$^{-1}$); 1775, 1710, 1670, 1630

NMR (DMSO-d$_6$, δppm); 1.34 (d, J=6.5 Hz, 3H, —CH$_3$), 2.8~3.5 (m, 2H, —CH$_2$—), 3.72 (br, 2H, 2- position —H$_2$), 4.0~4.9 (m, 3H, 3-position —CH$_2$—, —OCH<), 5.16 (d, J=5 Hz, 1H, 6-position —H), 5.78 (d×d, J=5 Hz, 8 Hz, 1H, 7-position —H), 7.0 (s, 1H, thiazole 5-position —H), 7.8~9.6 (br, 7H, —NH$_3^+$×2, —CO$_2$H), 9.54 (s, 1H, thiadiazole 5-position —H), 9.74 (d, J=8 Hz, 1H, —CONH—)

EXAMPLE 6

7-[2-(2-Aminothiazol-4-yl)-2-(2-amino-1-ethylethoxyimino)acetamido]-cephalosporanic acid trifluoroacetate (syn isomer)

(1) 3.5 g of 1-t-butoxycarbonylamino-2-phthalimidooxybutane as obtained in Example 2 (1) is treated in the same manner as in Example 3 (3) to give 1.57 g of 2-aminooxy-1-t-butoxycarbonylaminobutane.

IR (Neat, cm$^{-1}$); 3350, 1700, 1590

NMR (CDCl$_3$, δppm); 0.93 (t, J=7 Hz, 3H, —CH$_3$), 1.1~2.1 (m, 2H, —CH$_2$—), 1.46 (s, 9H, Boc—), 2.80~3.75 (m, 3H, >CHCH$_2$—), 4.55~5.85 (br, 3H, —NH$_2$, —NH—)

(2) 1.47 g of the product obtained in (1) is dissolved in 60 ml of 70% aqueous tetrahydrofuran solution. To this solution, 2.04 g of 2-(2-t-butoxycarbonylaminothiazol-4-yl)glyoxylic acid and 3 ml of saturated aqueous sodium carbonate are added, and this is followed by 1 hour of agitation at room temperature. After evaporation of tetrahydrofuran under reduced pressure, the residue is acidified to pH 3 with 10% citric acid and extracted with 150-ml and 50-ml portions of ethyl acetate. The organic layers are combined together, washed with a sodium chloride solution, and dried with anhydrous Glauber's salt. The solvent is evaporated under reduced pressure, and the residue is subjected to silica gel column chromatography and eluted with chloroform-methanol, whereafter the desired fraction is concentrated to give 1.69 g of 2-(2-t-butoxy-carbonylamino-1-ethylethoxyimino)-2-(2-t-butoxycarbonylaminothiazol-4-yl)acetic acid (syn isomer).

IR (Nujol, cm$^{-1}$); 1715, 1560

NMR (CDCl$_3$, δppm); 0.95 (t, J=7 Hz, 3H, —CH$_3$), 1.2~1.8 (m, 2H, —CH$_2$—), 1.37 (s, 9H, Boc—), 1.55 (s, 9H, Boc—), 3.2~3.6 (m, 2H, —CH$_2$—), 4.0~4.5 (m, 1H, —OCH<), 5.1~5.5 (br, 1H, —NH—), 7.23 (s, 1H, thiazole 5-position —H), 7.7~8.5 (br, 2H, —NH—, —CO$_2$H)

(3) 1.59 g of the product obtained in (2) and 1.27 g of benzhydryl 7-amino-cephalosporanate are dissolved in 50 ml of dry methylene chloride. To this solution, 0.84 ml of pyridine and 0.65 ml of phosphorus oxychloride are added at −12° C., and this is followed by 90 minutes of agitation at the same temperature. 450 ml of ethyl acetate is added, and this mixture is washed with 10% citric acid and a sodium chloride solution, and dried with anhydrous Glauber's salt. The solvent is evaporated under reduced pressure, and the residue is subjected to silica gel column chromatography and eluted with ethyl acetate-benzene, whereafter the desired fraction is concentrated to give 1.15 g of benzhydryl 7-[2-(2-t-butoxycarbonylamino-1-ethylethoxyimino)-2-(2-t-butoxycarbonylaminothiazol-4-yl)acetamido]-cephalosporanate (syn isomer).

IR (Nujol, cm$^{-1}$); 1785, 1715, 1540

NMR (DMSO-d$_6$, δppm); 0.91 (t, J=7 Hz, 3H, —CH$_3$), 1.1~1.8 (m, 2H, —CH$_2$—), 1.35 (s, 9H, Boc—), 1.48 (s, 9H, Boc—), 1.97 (s, 3H, CH$_3$CO—), 3.0~3.4 (m, 2H, —CH$_2$—), 3.60 (br, 2H, 2-position —H$_2$), 3.8~4.3 (m, 1H, —OCH<), 4.60~4.90 (ABq, J=18 Hz, 2H, —CH$_2$—), 5.25 (d, J=5 Hz, 1H, 6-position —H), 5.96 (d×d, J=5 Hz, 8 Hz, 1H, 7-position —H), 6.5~6.8 (br, 1H, —NH—), 6.89 (s, 1H, —CH<), 7.1~7.7 (m, 12H, phenyl, thiazole 5-position —H, —NH—), 9.53 (d, J=8 Hz, 1H, —CONH—)

(4) 450 mg of the product obtained in (3) is dissolved in 1.4 ml of anisole. To this solution, 11.3 ml of trifluoroacetic acid is added while cooling with ice, and this is followed by 3.5 hours of agitation. The reaction mixture is concetrated under reduced pressure, and the residue is poured into 70 ml of isopropyl ether. The separating solid is collected by filtration and dissolved in 4 ml of methanol.

This solution is poured into isopropyl ether to give 286 mg of the subject compound.

IR (KBr, cm$^{-1}$); 1770, 1670, 1630

NMR (DMSO-d$_6$, δppm); 1.00 (t, J=7 Hz, 3H, —CH$_3$), 1.4~1.9 (m, 2H, —CH$_2$—), 2.03 (s, 3H, —CH$_3$), 2.8~3.3 (m, 2H, —CH$_2$N<), 3.52 (br, 2H, 2-position —H$_2$), 4.0~4.5 (m, 1H, —OCH<), 4.70~5.00 (ABq, J=18 Hz, 2H, 3-position —CH$_2$—), 5.12 (d, J=5 Hz, 1H, 6-position —H), 5.80 (d×d, J=5 Hz, 1H, 7-position —H), 6.80 (s, 1H, thiazole 5-position —H), 6.0~8.5 (br, 6H, —NH$_3^+$, —NH$_2$, —CO$_2$H), 9.30 (d, J=8 Hz, 1H, —CONH—)

EXAMPLE 7

7-[2-(2-Aminothiazol-4-yl)-2-(2-amino-1-ethylethoxyimino)acetamido]-cephalosporanic acid dihydrochloride (syn isomer)

(1) 1 g of the product obtained in Example 2 (2) and 735 mg of hydrazinium dichloride are added to 5 ml of ethanol, and this is followed by 40 minutes of agitation. After removing the separating substance, this mixture is concentrated under reduced pressure. The residue is subjected to silica gel column chromatography and eluted with chloroform-methanol, whereafter 630 mg of 2-(2-aminothiazol-4-yl)-2-(2-t-butoxycarbonylamino-1-ethylethoxyimino)acetic acid (syn isomer) is obtained from the desired fraction.

IR (Nujol, cm$^{-1}$); 1680

NMR (DMSO-d$_6$, δppm); 0.5~1.1 (m, 3H, —CH$_3$), 1.1~1.9 (m, 2H, —CH$_2$—), 1.40 (s, 9H, Boc—), 2.8~3.4 (m, 2H, —CH$_2$N<), 3.7~4.3 (m, 1H, —CH<), 6.4~6.9 (m, 1H, —NH—), 6.82 (s, 1H, thiazole 5-position —H), 5.0~8.5 (br, 3H, —CO$_2$H, —NH$_2$)

(2) 400 mg of the product obtained in (1) and 364 mg of benzhydryl 7-aminocephalosporanate are dissolved in 12 ml of dry methylene chloride, and 0.18 ml of dicyclohexylamine and 0.24 ml of dimethylaniline are added at −15° C. While stirring this solution at the same temperature, 2 ml of a solution of 162 mg of phosphorus oxychloride in methylene chloride is added dropwise. After 1 hour agitation, this mixture is extracted with 50 ml of 10% citric acid and 100 ml of ethyl acetate. The organic layer is washed with aqueous sodium bicarbonate and a sodium chloride solution, after which it is dried with anhydrous Glauber's salt. The dried organic layer is concentrated under reduced pressure, and the residue is subjected to silica gel column chromatography and eluted with chloroform-methanol to give 300 mg of benzhydryl 7-[2-(2-aminothiazol-4-yl)-2-(2-t-butoxycarbonylamino-1-ethylethyoxyimino)acetamido]-cephaosporanate (syn isomer).

IR (Nujol, cm$^{-1}$); 1780, 1720, 1685

NMR (DMSO-d$_6$, δppm); 0.6~1.2 (m, 3H, —CH$_3$), 1.30 (s, 9H, Boc—), 1.2~1.8 (m, 2H, —CH$_2$—), 1.93 (s, 3H, CH$_3$CO—), 3.0~3.5 (m, 2H, —CH$_2$N<), 3.5~3.8

(m, 2H, 2-position —H$_2$), 3.8~4.3 (m, 1H, —CH<), 4.65, 4.90 (Abq, J=12 Hz, 2H, 3-position —CH$_2$—), 5.25 (d, J=5 Hz, 1H, 6-position —H), 5.95 (d×d, J=5 Hz, 8 Hz, 1H, 7-position —H), 6.70, 6.72 (s, s, 1H, thiazole 5-position —H), 6.90 (s, 1H, —CH<), 6.4~7.0 (br, 1H, —NH—), 7.0~7.8 (br, 2H, —NH$_2$), 7.3 (s, 10H, phenyl), 9.40 (d, J=8 Hz, 1H, —CONH—)

(3) 265 mg of the product obtained in (2) is dissolved in 0.53 ml of formic acid. To this solution, 0.73 ml of a 6.9 w/w% hydrogen chloride-formic acid solution is added at 10° C., and this is followed by 2 hours of agitation. This mixture is poured into 100 ml of diethyl ether. The separating solid is collected by filtration and dissolved in a small amount of methanol. This solution is again poured into 100 ml of diethyl ether to give 170 mg of the subject compound.

IR (Nujol, cm$^{-1}$); 1770, 1720

NMR (DMSO-d$_6$, δppm); 0.6~1.4 (m, 3H, —CH$_3$), 1.4~2.0 (m, 2H, —CH$_2$—), 2.03 (s, 3H, CH$_3$CO—), 2.8~3.5 (m, 2H, —CH$_2$N<), 3.5~4.0 (m, 2H, 2-position —H$_2$), 4.1~4.6 (m, 1H, —OCH<), 4.70, 5.05 (ABq, J=12 Hz, 2H, 3-position —CH$_2$—), 5.20 (d, J=5 Hz, 1H, 6-position —H), 5.85 (d×d, J=5 Hz, 8 Hz, 1H, 7-position —H), 6.95 (s, 1H, thiazole 5-position —H) 9.65, 9.70 (d, d, J=8 Hz, 1H, —CONH—) 6.5, 8.2 (br, br, 7H, —NH$_3^+$×2, —CO$_2$H)

EXAMPLE 8

7-[2-(2-Aminothiazol-4-yl)-2-(2-amino-1-ethylethoxyimino)acetamido]-cephalosporanic acid (syn isomer)

1 g of the product obtained in Example 7 is dissolved in 40 ml of water. This solution, after being acidified to pH 5.5 with sodium carbonate, is subjected to column chromatography with Diaion HP21 and eluted with water-acetonitrile, whereafter the desired fraction is lyophilized to give 490 mg of the subject compound.

IR (Nujol, cm$^{-1}$); 3200, 1775, 1735, 1670, 1605

NMR (DMSO-d$_6$, δppm); 0.88 (t, J=7 Hz, 3H, —CH$_3$), 1.2~2.0 (m, 2H, —CH$_2$—), 2.00 (s, 3H, CH$_3$CO—), 2.7~3.5 (m, 2H, —CH$_2$—), 3.2~3.6 (br, 2H, 2-position —H$_2$), 4.0~4.6 (m, 1H, —OCH<), 4.70, 4.95 (Abq, J=12 Hz, 2H, 3-position —CH$_2$—), 5.02 (d, J=5 Hz, 1H, 6-position —H), 5.5~5.9 (m, 1H, 7-position —H), 6.2~7.7 (br, 5H, —NH$_2$×2, —CO$_2$H), 6.77 (s, 1H, thiazole 5-position —H), 9.0~9.8 (br, 1H, —CONH—)

EXAMPLE 9

7-[2-(2-Aminothiazol-4-yl)-2-(2-amino-1-methylethoxyimino)acetamido]-3-(1-pyridiniummethyl)-3-cephem-4-carboxylic acid chloride dihydrochloride (syn isomer)

(1) To a mixture of 0.6 ml of ethyl acetate and 0.15 ml of dimethylformamide, 0.16 ml of oxalyl chloride is added at —8° C., and this is followed by 10 minutes of agitation. 5 ml of a solution of 562 mg of the product obtained in Example 1 (4) in ethyl acetate is added dropwise at —10° C. and this is followed by 30 minutes of agitation. Separately, 12 ml of tetrahydrofuran and 1.76 g of trimethylsilylacetamide are added to 600 mg of 7-amino-3-pyridiniomethyl-3-cephem-4-carboxylic acid perchlorate, and this is followed by 30 minutes of agitation at 10° C. To this solution, the reaction mixture prepared previously is added at —10° C., and this is followed by 1 hour of agitation. To this mixture, 120 ml of ethyl acetate and 60 ml of water are added. The separating substance is dissolved in aqueous sodium bicarbonate and combined with the aqueous layer. 200 ml of tetrahydrofuran is added and this mixture is acidified with citric acid. Sodium chloride is then added and this mixture is separeted to layers. The water layer is extracted with two 100-ml portions of tetrahydrofuran. The organic layers are combined together and washed with a sodium chloride solution. The washed mixture is dried with anhydrous magnesium sulfate, and the solvent is evaporated under reduced pressure, whereafter the rersidue is solidified with isopropyl ether to give 345 mg of 7-[2-(2-t-butoxycarbonylamino-1-methylethoxyimino)-2-(2-formamidothiazol-4-yl)acetamido]-3-pyridiniomethyl-3-cephem-4-carboxylic acid (syn isomer).

NMR (DMSO-d$_6$, δppm); 1.3 (d, J=5.5 Hz, 3H, —CH$_3$), 1.34 (s, 9H, Boc—), 3.0~3.8 (m, 4H, 2-position —H$_2$, —CH$_2$—), 4.0~4.5 (br, 1H, —OCH<), 5.22 (d, J=5 Hz, 1H, 6-position —H), 5.6 (brs, 2H, 3-position —CH$_2$—), 5.96 (d×d, J=5 Hz, 8.5 Hz, 1H, 7-position —H), 7.36, 7.4 (s, s, 1H, thiazole 5-position —H), 8.2~8.8 (m, 4H, pyridyl 3-, 4-, 5-position —H, —CHO), 8.9~9.3 (m, 2H, pyridyl 2-, 6-position —H), 9.54 (d, J=8.5 Hz, 1H, —CONH—), 12.6 (brs, 1H, —NH—)

(2) 290 mg of the product obtained in (1) is dissolved in 2.9 ml of methanol and 0.3 ml of concentrated hydrochloric acid is added at room temperature. After 2 hours of agitation, this mixture is poured into 30 ml of diethyl ether. The separating substance is collected by filtration, and 3.3 v/v% concentrated hydrochloric acid-formic acid is added while cooling with ice. After 40 minutes of agitation, this mixture is poured into 30 ml of diethyl ether. The separating substance is collected by filtration and dried to give 103 mg of the subject compound.

IR (Nujol, cm$^{-1}$); 1780, 1710, 1670, 1630

NMR (DMSO-d$_6$, δppm); 1.33 (d, J=5.5 Hz, 3H, —CH$_3$), 2.8~3.8 (m, 4H, 2-position —H$_2$, —CH$_2$—), 4.4~4.8 (br, 1H, —OCH<), 5.24 (d, J=5 Hz, 1H, 6-position —H), 5.63 (s, 2H, 3-position —CH$_2$—), 5.89 (d×d, J=5 Hz, 8.5 Hz, 1H, 7-position —H), 6.94 (s, 1H, thiazole 5-position —H), 6.5~9.5 (br, 7H, —NH$_3^{30}$×2, —CO$_2$H), 7.9~8.8 (m, 3H, pyridyl 3-, 4-, 5-position —H), 8.9~9.3 (m, 2H, pyridyl 2-, 6-position —H), 9.82 (d, J=8.5 Hz, 1H, —CONH—)

EXAMPLE 10

Sodium 7-[2-(2-aminothiazol-4-yl)-2-(2-amino-1-ethylethoxyimino)acetamido]-3-(N-carboxymethylpyridinio-4-yl)thiomethyl-3-cephem-4-carboxylate (syn isomer)

(1) 2.21 g of the product obtained in Example 2 (2) and 2.04 g of p-methoxybenzyl 7-amino-3-chloromethyl-3-cephem-4-carboxylate hydrochloride are added to 20 ml of dry methylene chloride. To this mixture, 1.28 ml of pyridine is added at —15° C. while stirring the mixture. A solution of 0.98 ml of phosphorus oxychloride in 5 ml of methylene chloride is added dropwise, and this is followed by 1 hour of agitation at the same temperature. This mixture is then extracted with 200 ml of ethyl acetate and 100 ml of 10% citric acid. The organic layer is washed with aqueous sodium bicarbonate and a sodium chloride solution, and dried with anhydrous Glauber's salt. The solvent is evaporated, and the residue is solidified with isopropyl ether-petroleum ether. The solid is subjected to silica gel column chromatography and eluted with chloroformmethanol to give 2.13 g of p-methoxybenzyl 7-[2-(2-formamidothiazol-4-yl)-2-(2-t-butoxycarbonylamino-1-ethylethoxyimino)acetamido]-3-chloromethyl-3-cephem-4-carboxylate (syn isomer).

IR (Nujol, cm$^{-1}$); 1790, 1690

NMR (DMSO-d$_6$, δppm); 0.7~1.3 (m, 3H, —CH$_3$), 1.35 (s, 9H, Boc—), 1.3~1.9 (m, 2H, —CH$_2$—), 3.0~3.5 (m, 2H, —CH$_2$N<), 3.70 (m, 2H, 2-position —H$_2$), 3.75 (s, 3H, —OCH$_3$), 3.8~4.3 (m, 1H, —OCH<), 4.50 (s, 2H, —CH$_2$Cl), 5.20 (s, 2H, —CO$_2$CH$_2$—), 5.23 (d, J=5 Hz, 1H, 6-position —H), 5.95 (d×d, J=5 Hz, 8 Hz, 1H, 7-position —H), 6.4~7.1 (br, 1H, —NH—), 6.90, 7.38 (A$_2$B$_2$, J=10 Hz, 4H, phenyl), 7.35, 7.37 (s, s, 1H, thiazole 5-position —H), 8.45 (s, 1H, —CHO), 9.50 (d, J=8 Hz, 1H, —CONH—), 12.58 (s, 1H, —NH—)

(2) 1.5 g of the product obtained in (1) is dissolved in 18 ml of dimethylformamido. To this solution, 586 mg of sodium iodide is added at 10° C., and this is followed by 20 minutes of agitation at the same temperature. To this mixture, 725 mg of N-(diphenylmethyloxycarbonylmethyl)pyridine-4-thione is added, and this is followed by 2 hours of agitation. This mixture is extracted with 300 ml of chloroform and 200 ml of a 2% sodium chloride solution, and the organic layer is washed with a sodium chloride solution and dried with anhydrous Glauber's salt. The dried organic layer is concentrated under reduced pressure, and the residue is solidified with isopropyl ether to give 2.23 g of p-methoxybenzyl 7-[2-(2-formamidothiazol-4-yl)-2-(2-t-butoxycarbonylamino-1-ethylethoxyimino)acetoamido]-3-(N-diphenylmethoxycarbonylmethyl-pyridinio-4-yl)thiomethyl-3-cephem-4-carboxylate (iodide (syn isomer).

IR (Nujol, cm$^{-1}$); 1780, 1710, 1670, 1630

NMR (DMSO-d$_6$, δppm); 0.6~1.2 (m, 3H, —CH$_3$), 1.2~1.9 (m, 2H, —CH$_2$—), 1.35 (s, 9H, Boc—), 3.0~3.5 (m, 4H, 2-position —H$_2$, —CH$_2$N<), 3.70 (s, 3H, —OCH$_3$), 3.8~4.3 (m, 1H, —OCH<), 4.40 (br, 2H, —CH$_2$S—), 5.20 (s, 2H, —OCH$_2$—), 5.22 (d, J=5 Hz, 1H, 6-position —H), 5.5~6.1 (m, 3H, 7-position —H, —CH$_2$CO$_2$—), 6.82, 7.32 (A$_2$B$_2$, J=10 Hz, 4H, phenyl), 6.90 (s, 1H, —CH<), 6.5~7.1 (br, 1H, —NH—), 7.3~7.6 (m, 11H, diphenyl, thiazole 5-position —H), 8.0, 8.8 (A$_2$B$_2$, J=6 Hz, 4H, pyridine), 8.5 (s, 1H, —CHO), 9.55 (d, J=8 Hz, 1H, —CONH—), 12.60 (s, 1H, —NH—)

(3) 1.5 g of the product obtained in (2) is dissolved in 15 ml of methylene chloride. To this solution, a solution of 0.6 ml of concentrated hydrochloric acid in 6 ml of methanol is added at room temperature, and this is followed by 2 hours of agitation. The reaction mixture is concentrated under reduced pressure and poured into isopropyl ether. The separating substance is dissolved in methanol and again solidified with isopropyl ether. This solid is added to 4.2 ml of anisol. To this mixture, 7 ml of trifluoroacetic acid is added at 5° C., and this is followed by 2 hours of agitation. This mixture is poured into 100 ml of diethyl ether, and the separating substance is collected by filtration and dissolved in 100 ml of water. This solution is adjusted to pH 7.7 with sodium bicarbonate, after which it is subjected to column chromatography with Diaion HP21 and eluted with water-acetonitrile, whereafter the desired fraction is lyophilized to give 200 mg of the subject compound.

IR (Nujol, cm$^{-1}$); 1765, 1630

NMR (D$_2$O, δppm); 0.7~1.2 (m, 3H, —CH$_3$), 1.45~1.95 (m, 2H, —CH$_2$—), 3.2~3.45 (m, 2H, —CH$_2$N<), 3.47, 3.75 (ABq, J=16 Hz, 2H, 2-position —H$_2$), 4.10, 4.45 (ABq, J=15 Hz, 2H, 3-position —CH$_2$—), 4.1~4.6 (m, 1H, —OCH<), 5.00 (s, 2H, —CH$_2$CO$_2$—), 5.16 (d, J=5 Hz, 1H, 6-position —H), 5.75 (d, J=5 Hz, 1H, 7-position —H), 6.98 (s, 1H, thiazole 5-position —H) 7.76, 8.32 (A$_2$B$_2$, J=6 Hz, 4H, pyridine)

EXAMPLE 11

Sodium 7-[2-(2-aminothiazol-4-yl)-2-(2-amino-1-ethylethoxyimino)acetamido]-3-(1-carboxymethyl-1,2,3,4-tetrazol-5-yl)-thiomethyl-3-cephem-4-carboxylate (syn isomer)

(1) 1.0 g of the product obtained in Example 10 (1) is dissolved in 20 ml of dry dimethylformamide. To this solution, 407 mg of sodium iodide is added at 5° C. while stirring the solution, and this is followed by 20 minutes of agitation. To this mixture, 244 mg of sodium salt of 1-carboxymethyl-5-mercapto-1,2,3,4-tetrazole is added, and this is followed by 1.5 hours of agitation at the same temperature. 200 ml of ethyl acetate is added, and this mixture is washed with 100 ml of 10% citric acid and a sodium chloride solution, and dried with anhydrous Glauber's salt. The solvent is evaporated and the residue is solidified with isopropyl ether. This solid is subjected to silica gel column chromatography and eluted with chloroform-methanol to give 890 mg of sodium salt of p-methoxybenzyl 7-[2-(2-formamidothiazol-4-yl)-2-(2-t-butoxycarbonylamino-1-ethylethoxyimino)acetamido]-3-(1-carboxymethyl-1,2,3,4-tetrazol-5-yl)-thiomethyl-3-cephem-4-carboxylate (syn isomer).

IR (Nujol, cm$^{-1}$); 1790, 1690

NMR (DMSO-d$_6$, δppm); 0.6~1.3 (m, 3H, —CH$_3$), 1.40 (s, 9H, Boc—), 1.3~1.9 (m, 2H, —CH$_2$—), 3.0~3.5 (m, 2H, —CH$_2$N<), 3.70 (br-s, 2H, 2-position —H$_2$), 3.78 (s, 3H, —OCH$_3$), 3.8~4.3 (m, 1H, —OCH<), 4.15, 4.65 (ABq, J=13 Hz, 2H, 3-position —H$_2$), 5.10 (s, 2H, —CH$_2$CO$_2$—), 5.20 (s, 2H, —CO$_2$CH$_2$—), 5.0~5.3 (m, 1H, 6-position —H), 5.90 (d×d, J=5 Hz, 8 Hz, 1H, 7-position —H), 6.5~7.1 (br, 1H, —NH—), 6.95, 7.35 (A$_2$B$_2$, J=10 Hz, 4H, phenyl), 7.35 (s, 1H, thiazole 5-position —H), 8.50 (s, 1H, —CHO), 9.50 (d, J=8 Hz, 1H, —CONH—), 12.60 (s, 1H, —NH—)

(2) 850 mg of the product obtained in (1) is dissolved in 8.5 ml of methanol. To this solution, 0.44 ml of concentrated hydrochloric acid at room temperature and this is followed by 1.5 hours of agitation. The reaction mixture is concentrated under reduced pressure and solidified with isopropyl ether. This solid is subjected to silica gel column chromatography and eluted with chloroform-methanol; the eluate is solidified with isopropyl ether and added to 2.5 ml of anisole. To this mixture, 4.2 ml of trifluoroacetic acid is added at 5° C., and this is followed by 2 hours of agitation. This mixture is poured into diethyl ether, and the separating substance is collected by filtration and dissolved in 50 ml of water. This solution is adjusted to pH 7.8 with sodium bicarbonate, after which it is subjected to column chromatography with Diaion HP-21 and eluted with water-acetonitrile, whereafter the desired fraction is lyophilized to give 150 mg of the subject compound.

IR (Nujol, cm$^{-1}$); 1780, 1670

NMR (DMSO-d$_6$, δppm); 0.6~1.3 (m, 3H, —CH$_3$), 1.3~2.0 (m, 2H, —CH$_2$—), 2.8~3.3 (m, 2H, —CH$_2$N<), 3.70 (br-s, 2H, 2-position —H$_2$), 3.8~4.3 (m, 1H, —OCH<), 4.20, 4.60 (ABq, J=13 Hz, 2H, 3-position —H$_2$), 4.85 (s, 2H, —CH$_2$CO$_2$—), 5.10 (d, J=5 Hz, 6-position —H), 5.80 (d×d, J=5 Hz, 8 Hz, 1H, 7-position —H), 6.0~8.0 (br, 4H, —NH$_2$×2), 6.85 (s, 1H,

EXAMPLE 12

7-[2-(2-Aminothiazol-4-yl)-2-(2-amino-1-ethylethoxyimino)acetamido]-3-vinyl-3-cephem-4-carboxylic acid dihydrochloride (syn isomer)

(1) 2.35 g of the product obtained in Example 2 (2) and 2.00 g of benzhydryl 7-amino-3-vinyl-3-cephem-4-carboxylate are suspended in 80 ml of dry methylene chloride. To this suspension, 1.81 ml of pyridine and 1.04 ml of phosphorus oxychloride are added at −12° C., and this is followed by 90 minutes of agitation. 320 ml of ethyl acetate is added, and this mixture is washed with sequential addition of 10% citric acid and a sodium chloride solution, and dried with anhydrous Glauber's salt. The solvent is evaporated under reduced pressure, and the residue is solidified with petroleum ether. This solid is subjected to silica gel column chromatography and eluted with chloroform-methanol, whereafter the desired fraction is concentrated to give 3.19 g of benzhydryl 7-[2-(2-formamidothiazol-4-yl)-2-(2-t-butoxycarbonylamino-1-ethylethoxyimino)acetamido]-3-vinyl-3-cephem-4-carboxylate (syn isomer).

IR (Nujol, cm$^{-1}$); 1790, 1695, 1545

NMR (DMSO-d$_6$, δppm); 0.97 (t, J=7 Hz, 3H, —CH$_3$), 1.36 (s, 9H, Boc—), 1.4~1.9 (m, 2H, —CH$_2$—), 3.0~3.4 (m, 2H, —CH$_2$—), 3.6~3.9 (br, 2H, 2-position —H$_2$), 3.8~4.4 (m, 1H, —CH<), 5.1~5.6 (m, 2H, 6-position —H, =C<$^H_H$), 5.7~6.2 (m, 2H, 7-position —H, =C<$^H_H$), 6.4~6.9 (m, 2H, —NH—, —CH=), 6.94 (s, 1H, —CH<), 7.1~7.6 (m, 11H, thiazole 5-position —H, phenyl), 8.47 (s, 1H, —CHO), 9.46 (d, J=8 Hz, —CONH—), 12.58 (s, 1H, —NH—)

(2) 2.00 g of the product obtained in (1) is treated in the same manner as in Example 2 (4) to give 1.29 g of 7-[2-(2-formamidothiazol-4-yl)-2-(2-t-butoxycarbonylamino-1-ethylethoxyimino)acetamido]-3-vinyl-3-cephem-4-carboxylic acid (syn isomer).

IR (Nujol, cm$^{-1}$); 1780, 1690

NMR (DMSO-d$_6$, δppm); 0.80~1.20 (m, 3H, CH$_3$—), 1.35 (s, 9H, Boc—), 1.48~2.20 (m, 2H, —CH$_2$—), 2.80~6.40 (br, 1H, —CO$_2$H), 3.00~3.50 (m, 2H, —CH$_2$—), 3.50~3.90 (m, 2H, 2-position —H$_2$), 3.90~4.40 (m, 1H, —CH<), 5.04~5.60

(m, 2H, 6-position —H, =C<$^H_H$), 5.62~6.10 (m, 2H, 7-position —H, =C<$^H_H$), 6.30~7.28 (m, 2H, —NH—, —CH=), 7.40 (s, 1H, thiazole 5-position —H), 8.48 (s, 1H, —CHO), 9.50 (d, J=8 Hz, 1H, —CONH—), 12.60 (s, 1H, —NH—)

(3) 600 mg of the product obtained in (2) is treated in the same manner as in Example 2 (5) to give 290 mg of the subject compound.

IR (Nujol, cm$^{-1}$); 1775, 1680, 1630

NMR (DMSO-d$_6$, δppm); 0.92 (t, J=7 Hz, 3H, —CH$_3$), 1.3~2.2 (m, 2H, —CH$_2$—), 3.0~3.5 (m, 2H, —CH$_2$—), 3.6~3.9 (br, 2H, 2-position —H$_2$), 4.1~4.7 (m, 1H, —CH<), 5.0~5.54

(m, 2H, 6-position —H, =C<$^H_H$), 5.54~6.1 (m, 2H, 7-position —H, =C<$^H_H$), 6.6~7.3 (m, 1H, —CH=), 6.99 (s, 1H, thiazole 5-position —H), 7.3~9.3 (m, 7H, —NH$_3^+$×2, —CO$_2$H), 9.5~10.0 (m, 1H, —CONH—)

EXAMPLE 13

7-[2-(2-Aminothiazol-4-yl)-2-(2-amino-1-ethylethoxyimino)acetamido]-3-[4-(2-carbamoylethyl)-1-pyridiniomethyl]-3-cephem-4-carboxylate (syn isomer)

(1) 5.22 g of the product obtained in Example 7 (2) is treated in the same manner as in Example 2 (4) to give 2.85 g of 7-[2-(2-aminothiazol-4-yl)-2-[2-t-butoxycarbonylamino-1-ethylethoxyimino)acetamido]-cephalosporanic acid (syn isomer).

IR (Nujol, cm$^{-1}$); 1780, 1690

NMR (DMSO-d$_6$, δppm); 0.98 (t, J=7 Hz, 3H, CH$_3$—), 1.37 (s, 9H, Boc—), 1.38~1.85 (m, 2H, —CH$_2$—), 2.03 (s, 3H, CH$_3$CO—), 3.00~3.36 (m, 2H, —CH$_2$N<), 3.40~3.74 (m, 2H, 2-position —H$_2$), 3.75~4.30 (m, 1H, —CH<), 4.63, 5.02 (ABq, J=12 Hz, 2H, 3-position —CH$_2$—), 5.16 (d, J=5 Hz, 1H, 6-position —H), 5.82 (d×d, J=5 Hz, 8 Hz, 1H, 7-position —H), 6.45~6.80 (br, 1H, —NH—), 6.66, 6.69 (s, s, 1H, thiazole 5-position —H), 6.95~7.56 (br, 2H, —NH$_2$), 9.38 (d, J=8 Hz, 1H, —CONH—), 10.00~12.10 (br, 1H, —CO$_2$H)

(2) 2.80 g of the product obtained in (1) is dissolved in 8.4 ml of a mixture of acetonitrile and water (3:1). To this solution, 3.43 g of sodium iodide and 1.03 g of 4-(2-carbamoylethyl)pyridine are added, and this is followed by 5 hours of agitation at 70° to 75° C. The acetonitrile is evaporated under reduced pressure. The residual solution is poured into 100 ml of acetone, and the separating substance is collected by filtration to give 2.66 g of crude 7-[2-(2-aminothiazol-4-yl)-2-(2-t-butoxycarbonylamino-1-ethylethoxy-imino)acetamido]-3-[4-(2-carbamoylethyl)-1-pyridiniomethyl]-3-cephem-4-carboxylate iodide (syn isomer). This crude substance is dissolved in 16.6 ml of 8 v/v% concentrated hydrochloric acid-formic acid and stirred for 20 minutes while cooling with ice. This solution is then poured into 200 ml of ether, and the separating substance is collected by filtration. The powder thus obtained is suspended in 50 ml of water. This suspension, after being adjusted to pH 4 to 5 with an aqueous solution of sodium bicarbonate, is subjected to column chromatography with Diaion HP21 and eluted with water-acetonitrile, whereafter the desired fraction is lyophilized to give 0.45 g of the subject compound.

IR (Nujol, cm$^{-1}$); 1770, 1660, 1630

NMR (D$_2$O, δppm); 0.70~1.20 (m, 3H, CH$_3$—), 1.45~2.05 (m, 2H, —CH$_2$—), 2.45~2.86 (t, J=7 Hz, 2H, —CH$_2$—), 2.90~3.65 (m, 6H, —CH$_2$—, —CH$_2$N<, 2-position —H$_2$), 3.35, 3.75 (ABq, J=17 Hz, 2H, 2-position —H$_2$), 4.10~4.58 (m, 1H, —CH<), 5.25 (d, J=5 Hz, 1H, 6-position —H), 5.18, 5.50 (ABq, J=14 Hz, 2H, 3-position —CH$_2$—), 5.84 (d, J=5 Hz, 1H, 7-position —H), 6.98 (s, 1H, thiazole 5-position —H), 7.86~8.73 (A$_2$B$_2$, J=8 Hz, 4H, pyridine)

EXAMPLE 14

7-[2-(2-Aminothiazol-4-yl)-2-(2-amino-1-cyclopropylethoxyimino)acetamido]-cephalosporanic acid dihydrochloride (syn isomer)

(1) 1.88 g of the product obtained in Example 3 (4) and 1.49 g of hydrazinium dichloride are added to 20 ml of ethanol, and this is followed by 2 days of agitation at room temperature. The separating substance is removed by filtration, and the filtrate is concentrated under reduced pressure. To the residue, 20 ml of chloroform is added, and this is followed by further filtration. The filtrate is concentrated under reduced pressure to give 1.74 g of 2-(2-aminothiazol-4-yl)-2-(2-t-butoxycarbonylamino-1-cyclopropylethoxyimino)acetic acid (syn isomer).

IR (Nujol, cm$^{-1}$); 1690, 1630

NMR (DMSO-d$_6$, δppm); 0.15~1.60 (m, 5H, cyclopropyl), 1.38 (s, 9H, Boc—), 3.10~3.80 (m, 3H, >CHCH$_2$—), 6.40~6.85 (br, 1H, —NH—), 6.95 (s, 1H, thiazole 5-position —H), 8.40~10.00 (br, 3H, —CO$_2$H, —NH$_2$)

(2) 1.74 g of the product obtained in (1) and 1.72 g of benzhydryl 7-aminocephalosporanate are treated in the same manner as in Example 1 (5) to give 1.6 g of benzhydryl 7-[2-(2-aminothiazol-4-yl)-2-(2-t-butoxycarbonylamino-1-cyclopropylethoxyimino)acetamido]-cephalosporanate (syn isomer).

IR (Nujol, cm$^{-1}$); 3350, 1790, 1740, 1730, 1690

NMR (DMSO-d$_6$, δppm); 0.16~1.50 (m, 5H, cyclopropyl), 1.37 (s, 9H, Boc—), 1.97 (s, 3H, —CH$_3$), 3.10~3.90 (m, 5H, >CHCH$_2$—, 2-position —H$_2$), 4.60, 4.90 (ABq, J=14 Hz, 2H, 3-position —CH$_2$—), 5.22 (d, J=5 Hz, 1H, 6-position —H), 5.96 (d×d, J=5 Hz, 8 Hz, 1H, 7-position —H), 6.69, 6.70 (s, s, 1H, thiazole 5-position —H), 6.88 (s, 1H, —CH<), 7.32 (s, 10H, phenyl), 9.40 (d, J=8 Hz, 1H, —CONH—)

(3) 1.54 g of the product obtained in (2) is treated in the same manner as in Example 7 (3) to give 1.12 g of the subject compound.

IR (Nujol, cm$^{-1}$); 1780, 1720, 1680, 1630

NMR (DMSO-d$_6$, δppm); 0.20~1.70 (m, 5H, cyclopropyl), 2.04 (s, 3H, —CH$_3$), 3.00~4.15 (m, 5H, >CHCH$_2$—, 2-position —H$_2$), 4.66, 5.06 (ABq, J=14 Hz, 2H, 3-position —CH$_2$—), 5.20 (d, J=5 Hz, 1H, 6-position —H), 5.86 (d×d, J=5 Hz, 8 Hz, 1H, 7-position —H), 6.99 (s, 1H, thiazole 5-position —H), 6.60~10.00 (br, 7H, —CO$_2$H, —NH$_3^+$×2), 9.60~10.00 (m, 1H, —CONH—)

EXAMPLE 15

7-[2-(2-Aminothiazol-4-yl)-2-(2-amino-1-methylethoxyimino)acetamido]-cephalosporanic acid dihydrochloride (syn isomer)

(1) 2 g of the product obtained in Example 1 (4) is treated in the same manner as in Example 14 (1) to give 1.85 g of 2-(2-aminothiazol-4-yl)-2-(2-t-butoxycarbonylamino-1-methylethoxyimino)acetic acid (syn isomer).

NMR (DMSO-d$_6$, δppm); 1.14 (d, J=7 Hz, 3H, —CH$_3$), 1.38 (s, 9H, Boc—), 2.90~3.40 (m, 2H, —CH$_2$—), 4.02~4.56 (m, 1H, —CH<), 5.00~7.80 (br, 4H, —CO$_2$H, —NH—, —NH$_2$), 6.94 (s, 1H, thiazole 5-position —H)

(2) 1.85 g of the product obtained in (1) and 1.96 g of benzhydryl 7-aminocephalosporanate are treated in the same manner as in Example 1 (5) to give 1.38 g of benzhydryl 7-[2-(2-aminothiazol-4-yl)-2-(2-t-butoxycarbonylamino-1-methylethoxyimino)acetamido]-cephalosporanate (syn isomer).

IR (Nujol, cm$^{-1}$); 3350, 1790, 1730, 1690

NMR (DMSO-d$_6$, δppm); 1.18 (d, J=7 Hz, 3H, —CH$_3$), 1.38 (s, 9H, Boc—), 1.97 (s, 3H, —CH$_3$), 3.00~3.40 (m, 2H, —CH$_2$—), 3.60 (br, 2H, 2-position —H$_2$), 4.00~4.40 (m, 1H, —CH<), 4.60, 4.92 (ABq, J=14 Hz, 2H, 3-position —CH$_2$—), 5.21 (d, J=5 Hz, 1H, 6-position —H), 5.93 (d×d, J=5 Hz, 8 Hz, 1H, 7-position —H), 6.47~6.90 (br, 1H, —NH—), 6.71 (s, 1H, thiazole 5-position —H), 6.89 (s, 1H, —CH<), 7.34 (s, 10H, phenyl), 9.43 (d, J=8 Hz, —CONH—)

(3) 730 mg of the product obtained in (2) is treated in the same manner as in Example 7 (3) to give 460 mg of the subject compound.

IR (Nujol, cm$^{-1}$); 1780, 1730, 1680, 1630

NMR (DMSO-d$_6$, δppm); 1.34 (d, J=7 Hz, 3H, —CH$_3$), 2.04 (s, 3H, —CH$_3$), 2.84~3.40 (m, 1H, —CH$_2$—), 3.60 (br, 2H, 2-position —Hz), 4.16~4.80 (m, 1H, —CH<), 4.68, 5.06 (ABq, J=14 Hz, 2H, 3-position —CH$_2$—), 5.16 (d, J=5 Hz, 1H, 6-position —H), 5.82 (d×d, J=5 Hz, 8 Hz, 1H, 7-position —H), 6.10~9.20 (br, 7H, —CO$_2$H, —NH$_3^+$×2), 6.98 (s, 1H, thiazole 5-position —H), 9.70 (d, J=8 Hz, 1H, —CONH—)

EXAMPLE 16

Sodium 7-[2-(2-aminothiazol-4-yl)-2-(2-amino-1-methylethoxyimino)acetamido]-3-(N-carboxymethylpyridinio-4-yl)thiomethyl-3-cephem-4-carboxylate (syn isomer)

(1) 3.0 g of the product obtained in Example 1 (4) and 2.72 g of p-methoxybenzyl 7-amino-3-chloromethyl-3-cephem-4-carboxylate are treated in the same manner as in Example 10 (2) to give 2.93 g of p-methoxybenzyl 7-[2-(2-formamidothiazol-4-yl)-2-(t-butoxycarbonylamino-1-methylethoxyimino)acetamido]-3-chloromethyl-3-cephem-4-carboxylate (syn isomer).

IR (Nujol, cm$^{-1}$); 1790, 1690

NMR (DMSO-d$_6$, δppm); 1.20 (d, J=7 Hz, 3H, —CH$_3$), 1.35 (s, 9H, Boc—), 3.0~3.5 (m, 2H, —CH$_2$N<), 3.5~3.9 (br, 2H, 2-position —H$_2$), 3.75 (s, 3H, —OCH$_3$), 3.8~4.3 (m, 1H, —OCH<), 4.50 (s, 2H, —CH$_2$Cl), 5.20 (s, 2H, —CO$_2$CH$_2$—), 5.24 (d, J=5 Hz, 1H, 6-position —H), 5.95 (d×d, J=5 Hz, 8 Hz, 1H, 7-position —H), 6.4~7.1 (br, 1H, —NH—), 6.90, 7.40 (A$_2$B$_2$, J=10 Hz, 4H, phenyl), 7.35 (s, 1H, thiazole 5-position —H), 8.45 (s, 1H, —CHO), 9.50 (d, J=8 Hz, 1H, —CONH—), 12.58 (s, 1H, —NH—)

(2) 2.9 g of the product obtained in (1) is treated in the same manner as in Example 10 (2) to give 4.22 g of p-methoxybenzyl 7-[2-(2-formamidothiazol-4-yl)-2-(2-t-butoxycarbonylamino-1-methylethoxyimino)acetamido]-3-(N-diphenylmethoxycarbonyl-methyl-pyridinio-4-yl)thiomethyl-3-cephem-4-carboxylate iodide (syn isomer).

IR (Nujol, cm$^{-1}$); 1780, 1680, 1630

NMR (DMSO-d$_6$, δppm); 1.20 (d, J=7 Hz, 3H, —CH$_3$), 1.38 (s, 9H, Boc—), 3.0~3.5 (m, 2H, —CH$_2$N<), 3.5~3.9 (br, 2H, 2-position —H$_2$), 3.70 (s, 3H, —OCH$_3$), 3.8–4.3 (m, 1H, —OCH<), 4.40 (br, 2H, —CH$_2$S—), 5.20 (s, 2H, —OCH$_2$—), 5.22 (d, J=5 Hz, 1H, 6-position —H), 5.5~6.2 (m, 3H, 7-position —H, —CH$_2$CO$_2$—), 6.5~7.1 (br, 1H, —NH—) 6.82, 7.32 (A$_2$B$_2$, J=10 Hz, 4H, phenyl), 6.90 (s, 1H, —CH<), 7.2~7.7 (m, 11H, diphenyl, thiazole 5-position —H), 8.0, 8.8 (A$_2$B$_2$, J=6 Hz, 4H, pyridine), 8.50 (s, 1H, —CHO), 9.55 (d, J=8 Hz, 1H, —CONH—), 12.60 (s, 1H, —NH—)

(3) 4.2 g of the product obtained in (2) is treated in the same manner as in Example 10 (3) to give 490 mg of the subject compound.

IR (Nujol, cm$^{-1}$); 1770, 1630

NMR (D$_2$O, δppm); 1.38 (d, J=7 Hz, 3H, —CH$_3$), 3.2~3.5 (m, 2H, —CH$_2$N<), 3.45, 3.75 (ABq, J=16 Hz, 2H, 2-position —Hz), 4.10, 4.45 (ABq, J=15 Hz, 2H, 3-position —CH$_2$—), 4.1~4.6 (m, 1H, —OCH<), 5.00 (s, 2H, —CH$_2$CO$_2$—), 5.17 (d, J=5 Hz, 1H, 6-position —H), 5.78 (d, J=5 Hz, 1H, 7-position —H), 7.00 (s, 1H, thiazole 5-position —H), 7.76, 8.32 (A$_2$B$_2$, J=6 Hz, 4H, pyridine)

EXAMPLE 17

7-[2-(2-Aminothiazol-4-yl)-2-((S)-2-amino-1-methylethoxyimino)acetamido]-cephalosporanic acid (syn isomer)

(1) 5.0 g of (R)-1-amino-2-propanol is treated in the same manner as in Example 2 (1) to give 17.3 g of (S)-1-t-butoxycarbonylamino-2-phthalimido-oxy-propane.

IR (Nujol, cm$^{-1}$); 3424, 1784, 1737, 1700, 1506

NMR (DMSO-d$_6$, δppm); 1.27 (d, J=7 Hz, 3H, —CH$_3$), 1.39 (s, 9H, Boc—), 2.9~3.5 (m, 2H, —CH$_2$—), 4.0~4.7 (m, 1H, —CH<), 6.2~6.9 (m, 1H, —NH—), 7.88 (s, 4H, phenyl), (2) 14.0 g of the product obtained in (1) is treated in the same manner as in Example 3 (3) to give 7.8 g of (S)-2-aminoxy-1-t-butoxycarbonylamino-propane.

I R (Neat, cm$^{-1}$); 3326, 2976, 2934, 1700, 1588, 1520

N M R (DMSO-d$_6$, δppm); 1.01 (d, J=7 Hz, 3H, —CH$_3$), 1.40 (s, 9H, Boc—), 2.80~3.25 (m, 2H, —CH$_2$—), 3.25~3.85 (m, 1H, —CH<), 5.75 (br, 2H, —NH$_2$), 6.30~6.85 (m, 1H, —NH—)

(3) 7.8 g of the product obtained in (2) is treated in the same manner as in Example 3 (4) to give 7.7 g of 2-(2-formamidothiazol-4-yl)-2-((S)-2-t-butoxycarbonylamino-1-methylethoxyimino)acetic acid (syn isomer).

IR (Nujol, cm$^{-1}$); 1740, 1699, 1545

NMR (DMSO-d$_6$, δppm); 1.22 (d, J=7 Hz, 3H, —CH$_3$), 1.39 (s, 9H, Boc—), 2.8~3.5 (m, 2H, —CH$_2$—), 4.0~4.6 (m, 1H, —CH<), 6.4~6.9 (m, 1H, —NH—), 7.52 (s, 1H, thiazole 5-position —H), 8.52 (s, 1H, —CHO), 9.8~13.3 (br, 1H, —CO$_2$H), 12.60 (s, 1H, —NH—)

(4) 7.7 g of the product obtained in (3) is treated in the same manner as in Example 7 (1) to give 7.1 g of 2-(2-aminothiazol-4-yl)-2-((S)-2-t-butoxycarbonylamino-1-methylethoxyimino)acetic acid (syn isomer).

IR (Nujol, cm$^{-1}$); 1687, 1631, 1558, 1537

NMR (DMSO-d$_6$, δppm); 1.23 (d, J=7 Hz, 3H, —CH$_3$), 1.39 (s, 9H, Boc—), 2.9~3.6 (m, 2H, —CH$_2$—), 4.0~4.7 (m, 1H, —CH<), 6.4~7.1 (m, 1H, —NH—), 7.04 (s, 1H, thiazole 5-position —H), 8.6~10.6 (br, 3H, —CO$_2$H, —NH$_2$)

(5) 7.1 g of the product obtained in (4) is treated in the same manner as in Example 7 (2) to give 6.6 g of benzhydryl 7-[2-(2-aminothiazol-4-yl)-2-((S)-2-t-butoxycarbonylamino-1-methylethoxyimino)acetamido]-cephalosporanate (syn isomer).

IR (Nujol, cm$^{-1}$); 3350, 1786, 1725, 1692, 1530

NMR (DMSO-d$_6$, δppm); 1.21 (d, J=6 Hz, 3H, —CH$_3$), 1.37 (s, 9H, Boc-), 1.98 (s, 3H, CH$_3$CO—), 2.98~3.38 (m, 2H, —CH$_2$N<), 3.62 (br, 22H, 2-position —H$_2$), 3.90~4.42(m, 1H, —CH<), 4.61, 4.83 (ABq, J=14 Hz, 2H, 3-position —CH$_2$—), 5.25 (d, J=5 Hz, 1H, 6-position —H), 5.95 (d×d, J=5 Hz, 8 Hz, 1H, 7-position —H), 6.40~6.85 (br, 1H, —NH—), 6.76 (s, 1H, thiazole 5-position —H), 6.94 (s, 1H, —CH<), 7.00~7.75 (br, 2H, —NH$_2$), 7.37 (s, 10H, phenyl), 9.50 (d, J=8 Hz, 1H, —CONH—)

(6) 6.6 g of the product obtained in (5) is suspended in 6.6 ml of anisole. To this suspension, 19.8 ml of trifluoroacetic acid is added while cooling with ice, and this is followed by 1.5 hours of agitation. The reaction mixture is poured into 400 ml of diethyl ether and the separating solid is collected by filtration. The solid is dissolved in 250 ml of water. This solution, after being adjusted to pH 7.1 with sodium bicarbonate, is subjected to column chromatography with Diaion HP21 and eluted with water-acetonitrile, whereafter the desired fraction is lyophilized to give 2.6 g of the subject compound.

IR (Nujol, cm$^{-1}$); 1769, 1735, 1536

NMR (DMSO-d$_6$, δppm); 1.28 (d, J=6 Hz, 3H, —CH$_3$), 2.00 (s, 3H, CH$_3$CO—) 3.08 (br, 2H, —CH$_2$N<), 3.38 (br, 2H, 2-position —H$_2$), 4.08~4.83 (m, 1H, —CH<), 4.90 (br, 2H, 3-position —CH$_2$—), 5.03 (d, J=5 Hz, 1 H, 6-position —H), 5.44~5.80 (m, 1H, 7-position —H), 6.79 (s, 1H, thiazole 5-position —H), 8.80~9.94 (br, 1H, —CONH—), 6.00~10.50 (br, 5H, —NH$_2$×2, —CO$_2$H)

EXAMPLE 18

7-[2-(2-Aminothiazol-4-yl)-2-((R)-2-amino-1-methylethoxyimino)acetamido]-cephalosporanic acid (syn isomer)

(1) 5.4 g of (S)-1-amino-2-propanol is treated in accordance with the method of Example 17 to give 5.4 g of the subject compound.

IR (Nujol, cm$^{-1}$); 1769, 1735, 1532

NMR (DMSO-d$_6$, δppm); 1.26 (d, J=6 Hz, 3H, —CH$_3$), 2.01 (s, 3H, CH$_3$CO—), 3.08 (br, 2H, —CH$_2$N<), 3.38 (br, 2H, 2-position —H$_2$), 4.00~4.80 (m, 1H, —CH<), 4.89 (br, 2H, 3-position —CH$_2$—), 5.04 (d, J=5 Hz, 1H, 6-position —H), 5.40~5.96 (m, 1H, 7-position —H), 6.81 (s, 1H, thiazole 5-position —H), 8.96~9.96 (br, 1H, —CONH—), 6.00~10.80 (br, 5H, —NH$_2$×2, —CO$_2$H)

EXAMPLE 19

Stereoisomer A of 7-[2-(2-aminothiazol-4-yl)-2-(2-amino-1-ethylethoxyimino)acetamido]-cephalosporanic acid (syn isomer)

(1) 14.14 g of the product of Example 6 (1) and 10.4 g of L-(+)-tartaric acid are dissolved in 70 ml of methanol. The methanol is evaporated under reduced pressure, and the residue is dissolved in 67 ml of tetrahydrofuran. To this solution, 3.5 ml of water and 107 ml of diethylether are added, and this is followed by 3 hours of crystallization at room temperature. The separating crystal is collected by filtration, whereby a 7.44 g crystal is obtained. This crystal is dissolved in 92.8 ml of tetrahydrofuran while heating. To this solution, 1.5 ml of water and 59.5 ml of diethyl ether are added, and the separating crystal is collected by filtration, whereby a 5.32 g crystal is obtained. To this crystal, 200 ml of ethyl acetate is added. The organic layer is washed with 100 ml of saturated aqueous sodium bicarbonate and 100 ml of a saturated sodium chloride solution, after which it is dried with anhydrous Glauber's salt and concentrated under reduced pressure to give 3.07 g of stereoisomer A of 2-aminoxy-1-t-butoxycarbonylamino-butane.

$[\alpha]_D^{30} = -4.6°$ (c=10, ethanol)
IR (Nujol, cm$^{-1}$); 3322, 1681
NMR (DMSO-d$_6$, δppm); 0.60~1.10 (m, 3H, —CH$_3$), 1.38 (s, 9H, Boc—), 1.10~1.70 (m, 2H, —CH$_2$—), 2.90~3.50 (m, 3H, >CHCH$_2$—), 5.75 (s, 2H, —NH$_2$), 6.30~6.80 (br, 1H, —NH—)

(2) 3.07 g of the product obtained in (1) is treated in the same manner as in Example 3 (4) to give 3.18 g of the stereoisomer A of 2-(2-formamidothiazol-4-yl)-2-(2-t-butoxycarbonylamino-1-ethylethoxyimino)acetic acid (syn isomer).

IR (Nujol, cm$^{-1}$); 1696, 1548
NMR (DMSO-d$_6$, δppm); 0.60~1.10 (m, 3H, 3H, —CH$_3$), 1.39 (s, 9H, Boc—), 1.10~1.90 (m, 2H, —CH$_2$—), 2.90~3.50 (m, 2H, —CH$_2$N<), 3.80-4.40 (m, 1H, —CH<), 5.60~9.50 (br, 1H, —CO$_2$H), 6.40~6.90 (m, 1H, —NH—), 7.51 (s, 1H, thiazole 5-position —H), 8.53 (s, 1H, —CHO), 12.62 (br, 1H, —NH—)

(3) 3.18 g of the product obtained in (2) is treated in the same manner as in Example 7 (1) to give 2.92 g of the stereoisomer A of 2-(2-aminothiazol-4-yl)-2-(2-2-t-butoxycarbonylamino-1-ethylethoxyimino)acetic acid (syn isomer).

IR (Nujol, cm$^{-1}$); 1683, 1631
NMR (DMSO-d$_6$, δppm); 0.60~1.10 (m, 3H, —CH$_3$), 1.37 (s, 9H, Boc—) 1.10~1.90 (m, 2H, —CH$_2$—), 2.80~3.50 (m, 2H, —CH$_2$N<), 3.80~4.50 (m, 1H, —CH<), 6.30~7.00 (br, 1H, —NH—), 7.03 (s, 1H, thiazole 5-position —H), 7.00~9.60 (br, 3H, —NH$_2$, —CO$_2$H)

(4) 2.92 g of the product obtained in (3) is treated in the same manner as in Example 7 (2) to give 1.76 g of the stereoisomer A of benzhydryl 7-[2-(2-aminothiazol-4-yl)-2-(2-t-butoxycarbonylamino-1-ethylethoxyimino)acetamido]-cephalosporanate (syn isomer)

IR (Nujol, cm$^{-1}$); 1786, 1723, 1690
NMR (DMSO-d$_6$, δppm); 0.60~1.10 (m, 3H, —CH$_3$), 1.37 (s, 9H, Boc—), 1.10~1.80 (m, 2H, —CH$_2$—), 1.97 (s, 3H, CH$_3$CO—), 2.90~3.40 (m, 2H, —CH$_2$N<), 3.40~3.80 (br, 2H, 2-position —H$_2$), 3.80~4.20 (m, 1H, —CH<), 4.63, 4.93 (ABq, J=13 Hz, 2H, 3-position —CH$_2$—), 5.25 (d, J=5 Hz, 1H, 6-position —H), 5.97 (d×d, J=5 Hz, 8 Hz, 1H, 7-position —H), 6.40~6.80 (br, 1H, —NH—), 6.74 (s, 1H, thiazole 5-position —H), 6.94 (s, 1H, —CH<), 7.00~7.70 (m, 12H, phenyl, —NH$_2$), 9.47 (d, J=8 Hz, 1H, —CONH—)

(5) 1.76 g of the product obtained in (4) is treated in the same manner as in Example 17 (6) to give 0.95 g of the subject compound.

$[\alpha]_D^{29} = +56°$ (c=1, 0.3N hydrochloric acid)
IR (Nujol, cm$^{-1}$); 1774, 1735, 1535
NMR (DMSO-d$_6$, δppm); 0.60~1.20 (m, 3H, —CH$_3$), 1.20~2.00 (m, 2H, —CH$_2$—), 2.00 (s, 3H, CH$_3$CO—), 2.70~3.40 (br, 2H, —CH$_2$N<), 3.00~3.70 (br, 2H, 2-position —H$_2$), 4.00~4.50 (m, 1H, —CH<), 4.74, 5.01 ABq, J=13 Hz, 2H, 3-position —CH$_2$—), 5.03 (d, J=5 Hz, 1H, 6-position —H), 5.40~5.80 (m, 1H, 7-position —H), 6.79 (s, 1H, thiazole 5-position —H), 6.00~8.50 (br, 5H, —NH$_2$×2, —CO$_2$H), 8.50~10.00 (br, 1H, —CONH—)

EXAMPLE 20

Stereoisomer B of 7-[2-(2-aminothiazol-4-yl)-2-(2-amino-1-ethylethoxyimino)acetamido]-cephalosporanic acid (syn isomer)

(1) The filtrate obtained in Example 19 (1) is concentrated under reduced pressure, and the residue is dissolved in 200 ml of ethyl acetate. This solution is washed with two 100-ml portions of saturated sodium bicarbonate and then with 100 ml of a saturated aqueous sodium chloride solution, after which it is dried with anhydrous Glauber's salt. Ethyl acetate is evaporated under reduced pressure. The residue and 7.13 g of D-(−)-tartaric acid are dissolved in 50 ml of methanol, and methanol is evaporated under reduced pressure. The residue is dissolved in 46 ml of tetrahydrofuran. To this solution, 2.4 ml of water and 74 ml of diethyl ether are added, and this is followed by 1 hour of crystallization at room temperature. The separating crystal is collected by filtration, whereby an 8.07 g crystal is obtained. This crystal is dissolved in 32.3 ml of tetrahydrofuran while heating. To this solution, 1.6 ml of water and 64.6 ml of diethyl ether are added, and the separating crystal is collected by filtration, whereby a 5.74 g crystal is obtained. To this crystal, 200 ml of ethyl acetate is added. The organic layer is washed with 100 ml of a saturated bicarbonate and 100 ml of a saturated aqueous sodium chloride solution, after which it is dried with anhydrous Glauber's salt and concentrated under reduced pressure to give 3.31 g of the stereoisomer B of 2-aminoxy-1-t-butoxycarbonylamino-butane.

$[\alpha]_D^{30} = +4.6°$ (C=10, ethanol)
IR (Nujol, cm$^{-1}$); 3326, 1688
NMR (DMSO-d$_6$, δppm); 0.60~1.10 (m, 3H, —CH$_3$), 1.38 (s, 9H, Boc—), 1.10~1.70 (m, 2H, —CH$_2$—), 2.90~3.50 (m, 3H, >CHCH$_2$—) 5.74 (s, 2H, —NH$_2$), 6.30~6.80 (br, 1H, —NH—)

(2) 2.97 g of the product obtained in (1) is treated in accordance with the methods of Example 19 (2) through (5) to give 0.98 g of the subject compound.

$[\alpha]_D^{29} = +91°$ (c=1, 0.3N hydrochloric acid)
IR (Nujol, cm$^{-1}$); 1763, 1735, 1656, 1537
NMR (DMSO-d$_6$, δppm); 0.60~1.10 (m, 3H, —CH$_3$), 1.30~2.00 (m, 2H, —CH$_2$—), 2.01 (s, 3H, CH$_3$CO—), 2.70~3.40 (br, 2H, —CH$_2$N<), 3.00~3.60 (br, 2H, 2-position —H$_2$) 4.00~4.50 (m, 1H, —CH<), 4.71, 5.00 (ABq, J=13 Hz, 2H, 3-position —CH$_2$—), 5.04 (d, J=5 Hz, 1H, 6-position —H), 5.40~5.80 (m, 1H, 7-position —H), 6.80 (s, 1H, thiazole 5-position —H), 7.00~7.50 (br, 2H, —NH$_2$), 8.70~9.80 (br, 1H, —CONH—), 2.70~6.00 (br, 3H, —NH$_2$, —CO$_2$H)

EXAMPLE 21

Pivaloyloxymethyl 7-[2-(2-aminothiazol-4-yl)-2-(2-amino-1-ethylethyoxyimino)acetamido]-cephalosporanate dihydrochloride (syn isomer)

(1) 662 mg of the product obtained in Example 13 (1) is dissolved in 3.6 ml of N,N-dimethylformamide. To this solution, 124 mg of potassium acetate is added, and this mixture is cooled to −10° C. 439 mg of pivaloyloxymethyl iodide is added, and this mixture is stirred for 2 hours at the same temperature. 200 ml of cold ethyl acetate is added, and this mixture is washed with 100 ml of cold water and 100 ml of a cold sodium chloride solution, and dried with anhydrous Glauber's salt. The dried solution is concentrated under reduced pressure, and the residue is subjected to silica gel column chromatography and eluted with chloroform-methanol to give 607 mg of pivaloyloxymethyl 7-[2-(2-aminothiazol-4-yl)-2-(2-t-butoxycarbonylamino-1-ethyl-ethoxyimino)acetamido]-cephalosporanate (syn isomer).

IR (Nujol, cm$^{-1}$); 3350, 1795, 1750, 1690, 1625
NMR (DMSO-d$_6$, δppm): 0.62~1.80 (m, 5H, —CH$_2$CH$_3$), 1.17 (s, 9H, —C(CH$_3$)$_3$), 1.37 (s, 9H, Boc—), 2.02 (s, 3H, —CH$_3$), 2.95~3.45 (m, 2H, —CH$_2$—), 3.59 (br, 2H, 2-position —H$_2$), 3.80~4.23 (m, 1H, —CH<), 4.63, 4.98 (ABq, J=13 Hz, 2H, 3-position —CH$_2$—), 5.19 (d, J=5 Hz, 1H, 6-position —H), 5.57~6.08 (m, 3H, 7-position —H, —CO$_2$CH$_2$—), 6.40~6.90 (br, 1H, —NH—), 6.67 (s, 1H, thiazole 5-position —H), 6.90~7.40 (br, 2H, —NH$_2$), 9.39 (d, J=8 Hz, 1H, —CONH—)

(2) 533 mg of the product obtained in (1) dissolved in 2.8 ml of formic acid. To this solution, 0.36 ml of a solution of 10.7N hydrogen chloride in ethanol is added while cooling with ice, and this is followed by 10 minutes of agitation. This mixture is poured into 200 ml of diethyl ether, and the separating solid is collected by filtration and dissolved in 2 ml of methanol. This solution is again poured into 200 ml of diethyl ether to give 491 mg of the subject compound.

IR (Nujol, cm$^{-1}$); 1785, 1750, 1680, 1635
NMR (DMSO-d$_6$, δppm); 0.66~1.08 (m, 3H, —CH$_3$), 1.18 (s, 9H, —C(CH$_3$)$_3$), 1.40~2.20 (m, 2H, —CH$_2$—), 2.04 (s, 3H, —CH$_3$), 2.82~3.42 (m, 2H, —CH$_2$—), 3.66 (br, 2H, 2-position —H$_2$), 4.10~4.62 (m, 1H, —CH<), 4.64, 5.02 (ABq, J=13 Hz, 2H, 3-position —CH$_2$—), 5.22 (d, J=5 Hz, 1H, 6-position —H), 5.60~6.20 (m, 3H, 7-position —H, —CO$_2$CH$_2$—), 6.60~9.00 (br, 6H, —N$^+$H$_3$×2), 6.98 (s, 1H, thiazole 5-position —H), 9.72, 9.76 (d, d, 1H, —CONH—)

EXAMPLE 22

Pivaloyloxymethyl 7-[2-(2-aminothiazol-4-yl)-2-(2-amino-1-methylethoxyimino)acetamido]-cephalosporanate dihydrochloride (syn isomer)

(1) To 612 mg of the product obtained in Example 15 (2), 2.0 g of phenol is added, and this is followed by 4 hours of agitation at 50° C. 100 ml of ethyl acetate is added, and this mixture is extracted with two 60-ml portions of a 5% aqueous solution of sodium carbonate, acidified with citric acid, and further extracted with three 100-ml portions of ethyl acetate. The ethyl acetate layer is washed with a sodium chloride solution, dried with anhydrous Glauber's salt, and concentrated under reduced pressure, after which it is solidified with isopropyl ether to give 330 mg of 7-[2-(2-aminothiazol-4-yl)-2-(2-t-butoxycarbonylamino-1-methylethoxyimino)acetamido]-cephalosporanic acid (syn isomer).

(2) 330 mg of the product obtained in (1) is treated in accordance with the method of Example 21 to give 240 mg of the subject compound.

IR (Nujol, cm$^{-1}$); 1970, 1750, 1680, 1630
NMR (DMSO-d$_6$, δppm); 1.18 (s, 9H, —C(CH$_3$)$_3$), 1.36 (d, J=7 Hz, 3H, —CH$_3$), 2.06 (s, 3H, —CH$_3$), 2.80~3.44 (m, 2H, —CH$_2$—), 3.66 (br, 2H, 2-position —H$_2$), 4.06~4.60 (m, 1H, —CH<), 4.66, 5.02 (ABq, J=13 Hz, 2H, 3-position —CH$_2$—), 5.22 (d, J=5 Hz, 1H, 6-position —H), 5.50~6.12 (m, 3H, 7-position —H, —CO$_2$CH$_2$—), 6.20~9.00 (br, 6H, —N$^+$H$_3$×2), 7.00 (s, 1H, thiazole 5-position —H), 9.82 (d, J=8 Hz, 1H, —CONH—)

EXAMPLE 23

7-[2-(5-Amino-1,2,4-thiadiazol-3-yl)-2-(2-amino-1-ethylethoxyimino)acetamido]-cephalosporanic acid dihydrochloride (syn isomer)

(1) 2.0 g of 2-(5-formamido-1,2,4-thiadiazol-3-yl)glyoxylic acid is treated in accordance with the methods of Example 2

(2) and Example 7 to give 130 mg of the subject compound.

IR (Nujol, cm$^{-1}$); 1775, 1720
NMR (DMSO-d$_6$, δppm); 0.55~1.40 (m, 3H, —CH$_3$), 1.30~2.00 (m, 2H, —CH$_2$—), 1.97 (s, 3H, CH$_3$CO—), 2.70~3.50 (m, 2H, —CH$_2$N<), 3.60 (br, 2H, 2-position —H$_2$), 4.00~4.60 (m, 1H, —CH<), 4.67, 4.93 (ABq, J=14 Hz, 2H, 3-position —CH$_2$—), 5.12 (d, J=5 Hz, 1H, 6-position —H), 5.78 (d×d, J=5 Hz, J=8.5 Hz, 1H, 7-position —H), 9.50 (d, J=8.5 Hz, 1H, —CONH—), 8.00~10.50 (br, 7H, —N$^+$H$_3$×2, —CO$_2$H)

EXAMPLE 24

7-[2-(2-Aminothiazol-4-yl)-2-(2-amino-1-ethylethoxyimino)acetamido]-cephalosporanic acid dihydrochloride (syn isomer)

(1) 2.0 g of the product obtained in Example 4 (1) is dissolved in 10 ml of pyridine. To this solution, 4.04 g of p-toluenesulfonyl chloride and 128 mg of dimethylaminopyridine are added, and this is followed by 15 hours of agitation at room temperature. 200 ml of ethyl acetate is added, and this mixture is washed with 200 ml of 10% citric acid and 200 ml of a sodium chloride solution, and dried with anhydrous Glauber's salt. The dried solution is concentrated under reduced pressure, subjected to silica gel column chromatography, and eluted with benzene-ethyl acetate, whereafter the desired fraction is concentrated to give 2.53 g of p-toluenesulfonic acid ester of 1-t-butoxycarbonylamino-2-butanol.

IR (Nujol, cm$^{-1}$); 3398, 1685, 1519, 1355, 1175
NMR (CDCl$_3$, δppm); 0.84 (t, J=7 Hz, 3H, —CH$_3$), 1.44 (s, 9H, Boc—), 1.33~1.90 (m, 2H, —CH$_2$—), 2.45 (s, 3H, —CH$_3$), 3.00~3.50 (m, 2H, —CH$_2$N<), 4.20~5.00 (m, 2H, —CH<, —NH—), 7.31, 7.78 (A$_2$B$_2$q, J=8 Hz, 4H, phenyl)

(2) 1.65 g of ethyl 2-(2-formamidothiazol-4-yl)-2-hydroxyiminoacetate (syn isomer) is dissolved in 30 ml of dimethylformamide. To this solution, 165 mg of sodium hydride is added, and this is followed by 10 minutes of agitation at room temperature. 2.5 g of the product obtained in (1) is then added, and this is followed by 15 hours of agitation at the same temperature. 200 ml of ethyl acetate is added, and this mixture is washed with 200 ml of a sodium chloride solution and dried with anhydrous Glauber's salt. The dried solution is concentrated under reduced pressure, subjected to silica gel column chromatography, and eluted with n-hexane-ethyl acetate, whereafter the desired fraciton is concentrated to give 1.3 g of ethyl 2-(2-formamidothiazol-4-yl)-2-(2-t-butoxycarbonylamino-1-ethylethoxyimino-)acetate) (syn isomer). This ester is dissolved in 13 ml of ethanol. To this solution, 3.1 ml of an aqueous solution of 2N sodium hydroxide is added, and this is followed by 2 hours of agitation at room temperature. This mixture is concentrated under reduced pressure. To this concentrate, 200 ml of ethyl acetate is added, and this mixture is washed with 100 ml of 10% citric acid and 100 ml of a sodium chloride solution, and dried with anhydrous Glauber's salt. The dried solution is concentrated under reduced pressure to give 1.1 g of 2-(2-formamidothiazol-4-yl)-2-(2-t-butoxycarbonylamino-1-ethylethoxyimino)acetic acid (syn isomer).

The IR and NMR spectra of this compound agreed with those of the compound obtained in Example 2 (2).

(3) 1.0 g of the product obtained in (2) is treated in accordance with the method of Example 7 to give 303 mg of the subject compound.

The IR and NMR spectra of this compound agreed with those of the subject compound of Example 7.

FORMULATION EXAMPLE 1

To an aqueous solution containing 1 g of the compound produced in Example 17 is added 78 mg of sodium hydroxide. The mixture is lyophilized and filled into a vial. When used, it is dissolved in 20 ml of distilled water to make a parenteral solution.

FORMULATION EXAMPLE 2

1 g of the compound produced in Example 17 and 135 mg of sodium carbonate are filled into a vial. When used, it is dissolved in 20 ml of distilled water to make a parenteral solution.

FORMULATION EXAMPLE 3

1 g of the compound produced in Example 10 is dissolved in 20 ml of distilled water to make a parenteral solution.

We claim:

1. A cephalosporin compound represented by formula (I):

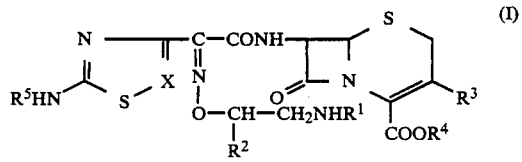

wherein $R^1$ and $R^5$ independently represent a hydrogen atom or an amino-protective group; $R^2$ represents a lower alkyl group or a cycloalkyl group with from 3 to 6 ring members; $R^3$ represents a hydrogen atom, a lower alkenyl group, a lower alkanoyloxymethyl group, a carbamoyloxymethyl group, a heterocyclic thiomethyl group or a heterocyclic methyl group; $R^4$ represents a hydrogen atom or an ester residue; a X represents CH or a nitrogen atom; each heterocyclic group is a 5- or 6-membered heterocyclic group; each hetero ring member is a nitrogen atom, a sulfur atom or an oxygen atom, each heterocyclic group has from 1 to 4 ring nitrogen atoms and is optionally substituted, and any substituent of a heterocyclic group is a member selected from the group consisting of an oxo group, a lower alkyl group, —$(CH_2)_xR^a$ (wherein $R^a$ is a hydroxyl group, methoxy group, a carbamoyl group, a carboxyl group, a dimethylamino group, a sulfonic acid group, or an unsubstituted heterocyclic group, as previously defined, an x is an integer from 0 to 2), —$(CH_2)_2$— and —$(CH_2)_3$—; or a pharmacologically-acceptable addition salt thereof.

2. A compound according to claim 1 wherein $R^3$ is a lower alkyl group.

3. A compound according to claim 1 wherein $R^3$ is a carbamoyloxymethyl group.

4. A compound according to claim 1 wherein $R^3$ is a heterocyclic thiomethyl group.

5. A compound according to claim 1 wherein $R^3$ is a heterocyclic methyl group.

6. A compound according to claim 1 wherein each heterocyclic group is an optionally-substituted member selected from the group consisting of tetrazolyl, triazolyl, thiazolyl, isothiazolyl, thiadiazolyl, pyridyl and pyrrolidinyl.

7. A cephalosporin compound as claimed in claim 1 wherein $R^3$ is a heterocyclic thiomethyl group or a heterocyclic methyl group, and the heterocycle of either heterocyclic group is a 5- or a 6-membered heterocycle which has from 1 to 4 ring nitrogen atoms and optionally has one or more additional ring heteroatoms, any such additional ring heteroatom being a sulfur atom or an oxygen atom.

8. The cephalosporin compound (I) as claimed in claim 1 having an alkanoyloxymethyl group for $R^3$, or a pharmacologically acceptable addition salt thereof.

9. The cephalosporin compound (I) as claimed in claim 1 having a 1,2,3-thiadiazol-5-yl group, 1,2,4-thiadiazol-5-yl group, 1,3,4-thiadiazol-2-yl group, 5-methyl-1,3,4-thiadiazol-2-yl group, N-methyl-pyridinium-2-yl group or N-carboxymethyl-pyridinium-4-yl group as the heterocycle in the heterocyclic thiomethyl group for $R^3$, or a pharmacologically acceptable addition salt thereof.

10. The cephalosporin compound (I) as claimed in claim 1 having pyridinium or 4-(2-carbamoylethyl)-pyridinium as the heterocyclic group in the heterocyclic methyl group for $R^3$, or a pharmacologically acceptable addition salt thereof.

11. The cephalosporin compound (I) as claimed in claim 1 wherein the specific rotation in its 7-[2-(2-aminothiazol-4-yl)-2-(2-amino-1-ethylethoxyimino)acetamido]-cephalosporanic acid (syn isomer) is +56°, or a pharmaceutically acceptable addition salt thereof.

12. The cephalosporin compound (I) as claimed in claim 1 wherein the specific rotation in its 7-[2-(2-aminothiazol-4-yl)-2-(2-amino-1-ethylethoxyimino)acetamido]-cephalosporanic acid (syn isomer) is +91°, or a pharmaceutically acceptable addition salt thereof.

13. The cephalosporin compound (I) or a pharmacologically acceptable addition salt thereof as claimed in claim 1 wherein the cephalosporin compound is:

7-[2-(2-aminothiazol-4-yl)-2-(2-amino-1-methylethoxyimino)acetamido]-3-(1,3,4-thiadiazol-2-yl)thiomethyl-3-cephem-4-carboxylic acid dihydrochloride (syn isomer), 7-[2-(2-aminothiazol-4-yl)-2-(2-amino-1-ethylethoxyimino)acetamido]-3-(1,3,4-thiadiazol-2-yl)thiomethyl-3-cephem-4-carboxylic acid dihydrochloride (syn isomer), 7-[2-(2-aminothiazol-4-yl)-2-(2-amino-1-cyclopropylethoxyimino)acetamido]-3-(1,3,4-thiadiazol-2-yl)thiomethyl-3-cephem-4-carboxylic acid dihydrochloride (syn isomer), 7-[2-(2-aminothiazol-4-yl)-2-((S)-2-amino-1-methylethoxyimino)acetamido]-3-(1,3,4-thiadiazol-2-yl)thiomethyl-3-cephem-4-carboxylic acid dihydrochloride (syn isomer), 7-[2-(2-aminothiazol-4-yl)-2-(2-amino-1-ethylethoxyimino)acetamido]-cephalosporanic acid trifluoroacetate (syn isomer), 7-[2-(2-aminothiazol-4-yl)-2-(2-amino-1-ethylethoxyimino)acetamido]-cephalosporanic acid dihydrochloride (syn isomer), 7-[2-(2-aminothiazol-4-yl)-2-(2-amino-1-ethylethoxyimino)acetamido]-cephalosporanic acid (syn isomer), 7-[2-(2-aminothiazol-4-yl)-2-(2-amino-1-methylethoxyimino)acetamido]-3-(1-pyridiniummethyl)-3-cephem-4-carboxylic acid chloride dihydrochloride (syn isomer), Sodium 7-[2-(2-aminothiazol-4-yl)-2-(2-amino-1-ethylethoxyimino)acetamido]-3-(N-carboxymethylpyridinio-4-yl)thiomethyl-3-cephem-4-carboxylate (syn isomer), Sodium 7-[2-(2-aminothiazol-4-yl)-2-(2-amino-1-ethylethoxyimino)acetamido]-3-(1-carboxymethyl-1,2,3,4-tetrazol-5-yl)thiomethyl-3-cephem-4-carboxylate (syn isomer), 7-[2-(2-aminothiazol-4-yl)-2-(2-amino-1-ethylethoxyimino)acetamido]-3-vinyl-3-cephem-4-carboxylic acid dihydrochloride (syn isomer), 7-[2-(2-aminothiazol-4-yl)-2-(2-amino-1-ethylethoxyimino)acetamido]-3-[4-(2-carbamoylethyl)-1-pyridiniomethyl]-3-cephem-4-carboxylic acid dihydrochloride (syn isomer), 7-[2-(2-aminothiazol-4-yl)-2-(2-amino-1-cyclopropylethoxyimino)acetamido]-cephalosporanic acid dihydrochloride (syn isomer), 7-[2-(2-aminothiazol-4-yl)-2-(2-amino-1-methylethoxyimino)acetamido]-cephalosporanic acid dihydrochloride (syn isomer), 7-[2-(2-aminothiazol-4-yl)-2-(2-amino-1-methylethoxyimino)acetamido]-3-(N-carboxymethylpyridinio-4-yl)thiomethyl-3-cephem-4-carboxylate (syn isomer), 7-[2-(2-aminothiazol-4-yl)-2-((S)-2-amino-1-methylethoxyimino)acetamido]-cephalosporanic acid (syn isomer), 7-[2-(2-aminothiazol-4-yl)-2-((R)-2-amino-1-methylethoxyimino)acetamido]-cephalosporanic acid (syn isomer), Stereoisomer A of 7-[2-(2-aminothiazol-4-yl)-2-(2-amino-1-ethylethoxyimino)acetamido]-cephalosporanic acid (syn isomer), Stereoisomer B of 7-[2-(2-aminothiazol-4-yl)-2-(2-amino-1-ethylethoxyimino)acetamido]-cephalosporanic acid (syn isomer), Pivaloyloxymethyl 7-[2-(2-aminothiazol-4-yl)-2-(2-amino-1-ethylethoxyimino)acetamido]-cephalosporanate dihydrochloride (syn isomer), Pivaloyloxymethyl 7-[2-(2-aminothiazol-4-yl)-2-(2-amino-1-methylethoxyimino)acetamido]-cephalosporanate dihydrochloride (syn isomer), or 7-[2-(5-amino-1,2,4-thiadiazol-3-yl)-2-(2-amino-1-ethylethoxyimino)acetamido]-cephalosporanic acid dihydrochloride (syn isomer).

14. A pharmaceutical composition, having a broad antibacterial spectrum and useful for treating bacteria-based infectious disease, comprising (a) an antibacterial-effective amount of at least one member selected from the group consisting of a cephalosporin compound as claimed in claim 1 and a pharmacologically acceptable addition salt thereof, and (b) pharmacologically acceptable additive.

15. A method of treating a host afflicted with a bacterial infection caused by Gram-positive bacteria, Gram-negative bacteria or Pseudomonas bacteria, which comprises administering to the host an effective amount of compound of claim 1 or of a pharmacologically acceptable addition salt thereof.

* * * * *